(12) United States Patent
Kumamoto et al.

(10) Patent No.: US 8,197,526 B2
(45) Date of Patent: *Jun. 12, 2012

(54) WARMING TOOL

(75) Inventors: Yoshiaki Kumamoto, Tochigi (JP); Masataka Ishikawa, Tochigi (JP); Takao Orii, Tokyo (JP)

(73) Assignee: Kao Corporation, Tokyo (JP)

( * ) Notice: Subject to any disclaimer, the term of this patent is extended or adjusted under 35 U.S.C. 154(b) by 938 days.

This patent is subject to a terminal disclaimer.

(21) Appl. No.: 10/556,136

(22) PCT Filed: May 7, 2004

(86) PCT No.: PCT/JP2004/006494
§ 371 (c)(1), (2), (4) Date: Jul. 28, 2006

(87) PCT Pub. No.: WO2004/098470
PCT Pub. Date: Nov. 18, 2004

(65) Prior Publication Data
US 2006/0276863 A1    Dec. 7, 2006

(30) Foreign Application Priority Data

May 9, 2003  (JP) ................................. 2003-131478
Oct. 10, 2003  (JP) ................................. 2003-352773
Apr. 20, 2004  (JP) ................................. 2004-124811

(51) Int. Cl.
*A61F 7/00* (2006.01)
*A61F 7/02* (2006.01)
*A61F 7/08* (2006.01)

(52) U.S. Cl. ........................... 607/114; 607/96; 607/111

(58) Field of Classification Search .................... 607/96, 607/108, 111, 114
See application file for complete search history.

(56) References Cited

U.S. PATENT DOCUMENTS

| 1,970,081 A | * | 8/1934 | Eisendrath | ..................... 126/204 |
| 4,516,564 A | * | 5/1985 | Koiso et al. | .............. 126/263.02 |
| 4,736,088 A | * | 4/1988 | Bart | .............................. 219/211 |

(Continued)

FOREIGN PATENT DOCUMENTS

JP        63-43532        3/1988

(Continued)

OTHER PUBLICATIONS

English language Translation of JP 01-201253, Yahara et al. (Aug. 14, 1989).*

(Continued)

*Primary Examiner* — Roy Gibson
*Assistant Examiner* — Kaitlyn Smith
(74) *Attorney, Agent, or Firm* — Oblon, Spivak, McClelland, Maier & Neustadt, L.L.P.

(57) ABSTRACT

A warming article having a heat generating main body (4). The heat generating main body (4) is composed of a heat generating element (2) having water vapor generating capability and an air permeable holder (3) for holding the heat generating element (2). The heat generating main body (4) is configured to expand with heat generation of the heat generating element (2). The amount of water vapor generated from the warming article is preferably 1.0 to 100 mg/(cm$^2 \cdot$10 min). The holder (3) preferably has a water vapor permeability of 1.5 to 10 kg/(m$^2 \cdot$24 hr). The heat generating element (2) is preferably a sheet molded by papermaking and containing an oxidizable metal, a moisture-retaining agent, and a fibrous material.

6 Claims, 5 Drawing Sheets

U.S. PATENT DOCUMENTS

| | | | |
|---|---|---|---|
| 5,050,596 A * | 9/1991 | Walasek et al. | 607/111 |
| 5,084,986 A * | 2/1992 | Usui | 36/2.6 |
| 5,425,975 A * | 6/1995 | Koiso et al. | 428/74 |
| 6,886,553 B2 * | 5/2005 | Yim | 126/263.02 |
| 6,974,470 B2 | 12/2005 | Tsunakawa et al. | |
| 7,950,385 B2 * | 5/2011 | Ohnishi et al. | 126/263.01 |
| 2001/0049546 A1 * | 12/2001 | Dvoretzky et al. | 607/108 |
| 2005/0000827 A1 | 1/2005 | Matsui et al. | |
| 2005/0028806 A1 | 2/2005 | Kumamoto et al. | |

FOREIGN PATENT DOCUMENTS

| | | |
|---|---|---|
| JP | 1-122930 U | 8/1989 |
| JP | 1-201253 | 8/1989 |
| JP | 5-170644 | 7/1993 |
| JP | 7-059809 | 3/1995 |
| JP | 7-255506 | 10/1995 |
| JP | 8-112303 | 5/1996 |
| JP | 2572621 | 10/1996 |
| JP | 10-216167 | 8/1998 |
| JP | 11-128260 | 5/1999 |
| JP | 11-508786 | 8/1999 |
| JP | 2000-50941 | 2/2000 |
| JP | 2000-139987 | 5/2000 |
| JP | 2001-170096 | 6/2001 |
| JP | 2002-58699 | 2/2002 |
| JP | 2002-78728 | 3/2002 |
| JP | 2003 332 | 1/2003 |
| JP | 2003-102761 | 4/2003 |
| JP | 2003-206479 | 7/2003 |
| WO | WO98/00077 | 1/1998 |

OTHER PUBLICATIONS

JP 2002-078728 JPO Machine Translation.*
U.S. Appl. No. 10/534,047, filed May 6, 2005, Kumamoto, et al.
U.S. Appl. No. 10/566,471, filed Jan. 31, 2006, Kumamoto, et al.

* cited by examiner

WARMING TOOL

TECHNICAL FIELD

The present invention relates to a warming article utilizing heat generation accompanying oxidation of an oxidizable metal with oxygen in air.

The present invention also relates to a heat generating shaped article utilizing heat generation accompanying oxidation of an oxidizable metal with oxygen in air, a warming article having the heat generating shaped article, and a method of producing the warming article.

BACKGROUND ART

Related art pertinent to warming articles making use of heat generation accompanying oxidation of an oxidizable metal with oxygen in air includes the warming tool described in JP-A-2003-332.

The warming tool comprises a cap-shaped base sheet which is adapted to be put on the head and a plurality of heat generating elements attached to the base sheet. The heat generating element of the warming tool loses flexibility and gets rough to the touch due to caking of the heat generating powder. Therefore, a warming article that is soft to the touch, conformable to a body, and useful in various applications has been awaited.

Related art pertinent to heat generating sheets utilizing heat generation accompanying oxidation of an oxidizable metal powder with oxygen in air includes the heat generating sheet disclosed in Japanese Patent No. 2572621. The sheet is produced by a papermaking technique using a composition of iron powder, activated carbon, an electrolyte, water, and a fibrous substance.

Applicant previously proposed a thin, heat generating molded article in JP-A-2003-102761. One of the characteristics of the molded article lies in that it is extremely thin and yet exhibits excellent heat generating characteristics as a heat generating element.

Separately from these heat generating elements of sheet form, heat generating shaped articles having a three-dimensional shape are desired in some applications. JP-T-1999-508786 proposes a three-dimensionally shaped heat generating element. Because the heat generating element is a heat cell having a given shape filled with an exothermic powder, it is difficult to obtain a three-dimensional shape appropriate for a specific application. Moreover, the technique requires a large quantity of the exothermic powder for obtaining desired heat generating performance and involves complicated steps for the production.

DISCLOSURE OF THE INVENTION

The present invention has been completed in the light of the above-described circumstances. A first object of the present invention is to provide a novel warming article that is soft to the touch, conformable to a body, and widely applicable.

A second object of the present invention is to provide a heat generating shaped article that is three-dimensionally shaped with good precision so as to be useful for various applications and a warming article having such a heat generating shaped article.

The first object of the present invention is accomplished by providing a warming article having a heat generating main body. The heat generating main body is composed of a heat generating element having water vapor generating capability and an air permeable holder for holding the heat generating element. The heat generating main body is configured to expand by water vapor generated with heat generation of the heat generating element.

The first object is also accomplished by providing another warming article having a heat generating main body. The heat generating main body is composed of a heat generating element having water vapor generating capability and an air permeable holder for holding the heat generating element. The amount of water vapor generated with heat generation of the heat generating element in the heat generating main body is 1.0 to 100 mg/(cm²·10 min).

The second object is accomplished by providing a heat generating shaped article that is a three-dimensionally shaped molded sheet. The molded sheet contains an oxidizable metal, a moisture-retaining agent, and a fibrous material and has a maximum stress of 0.3 to 5 MPa and a breaking elongation of 2.0 to 10%.

The present invention also provides a warming article having the heat generating shaped article of the present invention, in which the molded sheet is disposed between an air permeable sheet and an air impermeable sheet and three-dimensionally shaped together with the air permeable and the air impermeable sheets.

The present invention also provides a method of producing the warming article having the heat generating shaped article of the present invention. The method is characterized in that an electrolyte is incorporated into the heat generating shaped article.

BRIEF DESCRIPTION OF DRAWINGS

FIG. 5(a) and FIG. 5(b) schematically illustrate an embodiment of a warming article according to the present invention, in which FIG. 5(a) is a plan view, and FIG. 5(b) is a side view.

FIG. 6(a) and FIG. 6(b) both show a fragmentary cross-section of the embodiment of FIGS. 5(a) and 5(b), in which FIG. 6(a) is a fragmentary enlarged cross-section of the warming article, and FIG. 6(b) is a fragmentary enlarged cross-section of the heat generating shaped article.

DETAILED DESCRIPTION OF THE INVENTION

The present invention will be described based on its preferred embodiments with reference to the accompanying drawings.

FIGS. 1 through 4 show a first embodiment of the warming article according to the present invention. In the figures, numeral 1 indicates a warming article.

Figure 1:
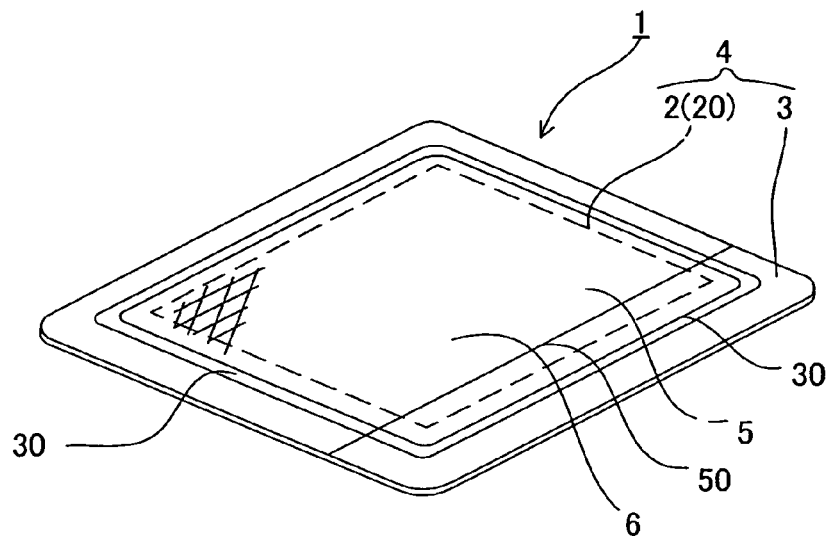
FIG. 1 is a perspective schematically illustrating an embodiment of a warming article according to the present invention.

As illustrated in FIG. 1, the warming article 1 has a heat generating main body 4. The heat generating main body 4 is composed of a heat generating element 2 having water vapor generating capability and an air-permeable holder 3. The heat generating main body 4 can be configured to expand by the water vapor generated by the heat generation of the heat generating element 2.

The warming article 1 of the first embodiment has a receiving part 5 for receiving a part of a body being inserted. The warming article 1 has a receiving part-forming member 6 joined to the upper side of the heat generating main body 4 to form the receiving part 5 having an insertion opening 50 on the outer side of the heat generating main body 4.

The temperature reached by the warming article is preferably 30° to 100° C., more preferably 35° to 60° C. This temperature is measured as follows. The warming article is placed in, e.g., a 4.2-liter closed chamber having a relative humidity of 1% or lower while feeding 5.0 l/min of dry air into the chamber to induce heat generating reaction. The temperature of the lower side of the warming article measured with a thermocouple is the temperature reached by the warming article. The reachable temperature can freely be designed by the formulation of the components or the layer structure (described later) according to the purpose, that is, whether a steep temperature rise is desired or a long duration of heat generation at a relatively low temperature is desired, and the like.

It is desirable for the warming article of the present invention to generate 1 to 100 mg, more desirably 5.0 to 50.0 mg, of water vapor per unit area ($cm^2$) for 10 minutes. The amount of water vapor generated ($mg/cm^2 \cdot 10$ min) is obtained by measuring the humidity having changed by the generated water vapor. Similarly, to the reachable temperature, the amount of water vapor produced can freely be designed by the formulation of the components and the layer structure (described later) according to the purpose, that is, whether a steep temperature rise is desired or a long duration of heat generating reaction at a relatively low temperature is desired, and the like.

The whole thickness of the warming article 1 is preferably 0.1 to 10 mm, more preferably 0.3 to 5.0 mm. Within this thickness range, the warming article 1 is portable, soft and flexible and therefore very convenient to use and comfortable to use. Where the warming article is designed to expand by the water vapor generated by the heat generation of the heat generating element 2, the thermal expansion will create a pleasant feeling of pressure inside the receiving part during use.

Where the warming article is configured to expand by the water vapor generated by the heat generation of the heat generating element, a favorable range of the volume expansion ratio of the warming article (the heat generating main body in this particular embodiment) varies depending on the intended use. From the aspect of an agreeable touch and a moderate feeling of pressure (feeling of tightness), a volume expansion ratio is preferably about 1.5 to 10000, more preferably about 3 to 7000. The volume expansion ratio is determined, for example, as follows. A container of a given capacity (e.g., a 30 cm side cubic container with the top open) is filled with ultrafine expanded beads (hereinafter "expanded beads"). After emptying the container, a warming article (a heat generating main body in the present embodiment) before or after heat generation is placed in the container, and the expanded beads are returned into the container to completely fill the space. The weight of the remainder of the expanded beads that are not put in the container is measured and divided by the density to obtain the volume of the sample before or after heat generation. Dividing the volume of the sample after heat generation by that before heat generation gives the volume expansion ratio of the sample. The "density" is obtained by dividing the weight of the expanded beads solely filling the container by the volume of the container. In a more convenient way, a warming article (a heat generating main body in the present embodiment) before or after heat generation is put in a container containing a predetermined amount of water. The volume expansion ratio is obtained from the difference in volume.

In order for the heat generating main body to expand, it is preferred for the warming article of the present invention to have a water vapor permeability of 1.5 to 10 $kg/(m^2 \cdot 24$ hr$)$, more preferably 2 to 8 $kg/(m^2 \cdot 24$ hr$)$, and an air permeability of 10 to 5000 sec/100 ml, more preferably 30 to 1000 sec/100 ml. The water vapor permeability of the heat generating main body is a value measured in accordance with JIS Z0208. Unless otherwise specified, "air permeability" is an Oken type air permeability value, expressed in time required for 100 ml of air to pass through an area of 645 $mm^2$.

The heat generating element 2 of the warming article 1 according to the present embodiment is composed of a sheet 20 prepared by papermaking. The sheet 20 contains an oxidizable metal, a moisture-retaining agent, a fibrous material, and water (a sheet 20 free from an electrolyte and water will be called a heat generating intermediate sheet 20, and a sheet 20 containing an electrolyte (hereinafter described) and water will be called a heat generating sheet 20). The heat generating element 2 of the warming article 1 according to the first embodiment is a stack of two heat generating sheets 20 (see FIG. 2).

The heat generating intermediate sheet 20 preferably contains at least 50% by weight, more preferably 70% by weight or more, even more preferably 80% by weight or more, of components other than the fibrous material. Where the proportion of the components other than the fibrous material is 50% by weight or more, the temperature will rise to a degree that is felt hot on touching with fingers, etc. While it is desirable that the proportion of the components other than the fibrous material be increased as much as possible, the upper limit would be 98% by weight for securing sufficient strength to maintain fabricability of the heat generating intermediate sheet 20. The proportion of the components other than the fibrous material is measured as follows.

The proportion of the components other than the fibrous material in the heat generating intermediate sheet 20 is calculated from the solids weight and composition of a raw material composition and the dry weight of the heat generating intermediate sheet 20 according to formula:

$$b=(Mh/Ms)\times(100-a)$$

wherein
b: content of components other than fibrous material in heat generating intermediate sheet
Mh: dry weight of heat generating intermediate sheet
Ms: solids weight of raw material composition
a (%): percentage of fibrous material in solids content of raw material composition The oxidizable metal for use in the present invention can be of any kind that is commonly employed in this type of heat generating molded articles. The oxidizable metal is preferably in the form of powder or fiber from the standpoint of ease in handling and molding capabilities.

Oxidizable metals in the form of powder include iron powder, aluminum powder, zinc powder, manganese powder, magnesium powder, and calcium powder etc. Iron powder is preferred among them in view of ease in handling, safety, and competitive production cost. Taking fixability onto the fibrous material and reaction controllability into consideration, the oxidizable metal powder preferably has a particle size of 0.1 to 300 μm. The term "particle size" as used herein means a maximum length of a powder particle or an average particle size measured by dynamic light scattering method, a laser diffraction method, and the like. It is more preferred to use powder containing at least 50% by weight of particles having a particle size of 0.1 to 150 µm.

Oxidizable metals in the form of fiber include steel fiber, aluminum fiber, and magnesium fiber etc. Steel fiber and aluminum fiber are preferred for their ease in handling, safety, and low cost. The fibrous oxidizable metal preferably has a length of 0.1 to 50 mm and a thickness of 1 to 1000 µm, from the viewpoint of molding capabilities, mechanical strength and surface smoothness of the resulting sheet, and heat generating performance.

The heat generating intermediate sheet 20 preferably contains 10% to 95% by weight, more preferably 30% to 80% by weight, of the oxidizable metal. With the oxidizable metal content being 10% by weight or more, the heat generating sheet 20 can heat up to such a degree that is felt hot on touching with fingers, etc. Since the proportion of the fibrous material and a binding component (hereinafter described) as sheet-forming components is held low, the heat generating sheet is prevented from getting hard and uncomfortable in use. With the oxidizable metal content being 95% by weight or less, the following advantages are offered. Formation of an oxide layer (e.g., of the oxidizable metal) on the surface of the heat generating sheet 20, which can impair air permeability, is suppressed. As a result, oxidation reaction occurs easily in the inside of the sheet to increase the temperature. The sheet is prevented from becoming too hard due to expansion and setting of the oxidizable metal as a result of oxidation reaction, and the sheet enjoys a long duration of heat generation. Sufficient supply of water by the moisture-retaining agent is assured. Fall-off of the oxidizable metal is minimized. A sufficient proportion of the fibrous material and the binding component (e.g., a flocculant) as sheet-forming components are secured to maintain mechanical strength, such as flexural strength and tensile strength. The oxidizable metal content in the heat generating sheet 20 can be measured by determination of ash in accordance with JIS P8128 or with a thermogravimetric analyzer. An iron content can also be determined by vibrating sample magnetization measurement making use of the magnetization phenomenon in an external magnetic field.

The moisture-retaining agent for use in the invention can be of any kind that is customarily employed in molded heat generating elements. The moisture-retaining agent has a water retaining function combined with a function as an agent for retaining and supplying oxygen to the oxidizable metal. Such a moisture-retaining agent includes activated carbon (including coconut shell charcoal, charcoal powder, bituminous coal, peat, and lignite), carbon black, acetylene black, graphite, zeolite, pearlite, vermiculite, silica, cancrinite, and fluorite etc. Preferred of them is activated carbon in view of its water retaining capability, oxygen feeding capability, and catalyzing ability. The moisture-retaining agent preferably has a powder form with a particle size ranging from 0.1 to 500 µm for providing effective contact with the oxidizable metal. It is more preferred to use powder containing at least 50% by weight of particles having a particle size of 0.1 to 200 µm. Moisture-retaining agents of other forms are also usable. For example, those of fibrous form such as activated carbon fiber can be used.

The heat generating intermediate sheet 20 preferably contains 0.5% to 60% by weight, more preferably 1% to 50% by weight, of the moisture-retaining agent. With at least 0.5% by weight of the moisture-retaining agent, the heat generating sheet 20 retains a sufficient amount of water for making the oxidizable metal continue being oxidized to generate heat to such a degree that can be felt warmer than a human body temperature. Furthermore, the air permeability of the heat generating sheet 20 is not impaired so that satisfactory oxygen supply is secured to promise high heat generation efficiency. With the moisture-retaining agent content being 60% by weight or less, the heat capacity of the heat generating sheet 20 is not so high for the heat value of generated heat. A temperature rise enough for a user to feel warmed can thus result. Fall-off of the moisture-retaining agent can be prevented. Furthermore, a sufficient proportion of the fibrous material and the binding component as sheet forming components are secured to maintain mechanical strength, such as flexural strength and tensile strength.

The fibrous material which can used includes natural fibers and synthetic fibers. The natural fibers include plant fibers, such as cotton, kapok fiber, wood pulp, non-wood pulp, peanut protein fiber, corn protein fiber, soybean protein fiber, mannan fiber, rubber fiber, hemp, Manila fiber, sisal fiber, New Zealand flax, Luo Buma, coconut, rush, and straw; animal fibers, such as wool, goat hair (including mohair and cashmere), alpaca, angora, camel, vicuna, silk, down, small feather, alginate fiber, chitin fiber, and casein fiber; and mineral fibers, such as asbestos. The synthetic fibers include semi-synthetic ones, such as cellulose diacetate fiber, cellulose triacetate fiber, oxidized acetate fiber, promix fiber, chlorinated rubber, and rubber hydrochloride, metal fibers, carbon fiber, and glass fiber. Additionally included are single-component fibers made of polyolefin (e.g., high-density polyethylene, medium-density polyethylene, low-density polyethylene or polypropylene), polyester, polyvinylidene chloride, starch, polyvinyl alcohol or polyvinyl acetate, a copolymer comprising monomers of these homopolymers, or a modified product of the homo- or copolymer; and core/sheath conjugate fibers having the above-recited resin component as a sheath. Of these synthetic fibers, polyolefin fibers and modified polyester fibers are preferably used for high bonding strength between individual fibers, high ability to form a three-dimensional network structure on fusion bonding of individual fibers, and a lower melting point than the ignition point of pulp fiber. Synthetic fibers of fibrillated polyolefins are also preferred for good fixation of the oxidizable metal and the moisture-retaining agent. The above-recited fibrous materials can be used either individually or as a combination of two or more thereof. Recycled products of these fibrous materials are also useful. Among these fibrous materials particularly preferred are wood pulp and cotton in view of their fixing capabilities for the oxidizable metal and the moisture-retaining agent, flexibility of the resulting molded sheet, oxygen permeability of the resulting sheet owing to the presence of interstices among fibers, and the cost of production.

It is preferred for the fibrous material to have a CSF (Canadian Standard Freeness) of 600 ml or less, more preferably 450 ml or less. Fibrous materials having a freeness of 600 ml or less shows satisfactory ability to fix the oxidizable metal, the moisture-retaining agent, etc. and to hold a prescribed formulation thereby to provide a warming article with excellent heat generating performance. Satisfactory molding properties, such as uniformity of sheet thickness, are obtained. Owing to the satisfactory fixing and holding ability of the fibrous material, fall-off of the oxidizable metal and the moisture-retaining agent is prevented, entanglement between the fibrous material and these components is obtained, and bonding strength relying on hydrogen bonding is obtained. As a result, the sheet exhibits mechanical strength, such as flexural strength and tensile strength, and good fabricability.

It is desirable for the fibrous material to have as low a CSF as possible. In general papermaking using pulp fiber as a sole fibrous material and small contents of other components, a CSF less than 100 ml means very poor freeness making dewatering difficult. It can follow that the resulting sheet has thickness unevenness or suffers from molding defects such as burst of blisters on drying. In the present invention, on the other hand, the presence of the components other than the fibrous material in high proportions contributes to optimization of freeness and provides a heat generating sheet with a uniform thickness. A lower CSF indicates a higher fibril content, and a higher fibril content secures better fixation of the components other than the fibrous material on the fibrous material, which results in high sheet strength.

The CSF of a fibrous material can be controlled by the degree of beating or blending fibers different in CSF.

The fibrous material preferably has a negative surface charge. A fibrous material with a more strongly negatively charged surface has better capability of fixing and holding the particulate components including the oxidizable metal, the moisture-retaining agent to provide a paper molded product with higher heat generating performance. The amount of the particulate components lost in the waste water in wet papermaking processing, which can adversely affect the productivity and lead to environmental pollution, can be minimized. The amount of the surface charge of the fibrous material is measured by colloid titration. The same applies to zeta potential of the fibrous material. "Zeta potential" is an apparent potential at the shear plane separating a charged particle and a solution, which can be determined by streaming potential measurement or electrophoresis measurement.

The fibrous material preferably has an average length of 0.1 to 50 mm, more preferably 0.2 to 20 mm. With the average fiber length falling within that range, sufficient mechanical strength (such as flexural strength and tensile strength) of the heat generating sheet 20 is secured. The resulting fiber web is prevented from becoming so dense as to impair air permeability. That is, oxygen is supplied smoothly to secure excellent heat generating performance. The fibrous material is uniformly dispersed in the heat generating sheet 20, resulting in uniform mechanical strength and uniform sheet thickness. In addition, the fiber distance is moderate to catch and hold the oxidizable metal, the moisture-retaining agent, and the like, not allowing these components to fall off.

The fibrous material content in the heat generating intermediate sheet 20 is preferably 2% to 50% by weight, more preferably 5% to 40% by weight. Where the content is 2% by weight or more, the components including the oxidizable metal and the moisture-retaining agent are prevented from falling off, and the heat generating sheet 20 becomes soft. With the fibrous material content being 50% by weight or less, the heat capacity of the heat generating sheet 20 is not so high for the amount of heat generated, and a sufficient rise in temperature is obtained. Furthermore, a sufficient proportion of the components in the heat generating sheet 20 is secured to obtain desired heat generating performance.

The fibrous material content and the oxidizable metal content can be measured with, for example, a thermogravimetric analyzer. Subtracting these contents from the total weight gives the content of the moisture-retaining agent.

The heat generating sheet 20 can contain a flocculant as hereinafter described.

If desired, the heat generating sheet 20 can contain additives commonly used in papermaking, such as sizes, colorants, strengthening agents, yield improvers, loading materials, thickeners, pH control agents, bulking agents and the like with no particular limitation. The amounts of the additives to be added can be selected appropriately according to the kinds.

The heat generating sheet 20 preferably contains an electrolyte. The electrolyte to be added can be of any kind chosen from those commonly used in this type of molded heat generating elements. Examples of useful electrolytes include sulfates, carbonates, chlorides or hydroxides of alkali metals, alkaline earth metals, heavy metals or the like. Preferred of them are chlorides, such as sodium chloride, potassium chloride, calcium chloride, magnesium chloride, iron (I) or (II) chloride and etc. for their electrical conductivity, chemical stability, and low production cost. These electrolytes can be used either individually or as a combination of two or more thereof.

The electrolyte is suitably added in an amount of 0.5% to 30% by weight, more preferably 1% to 25% by weight, based on the water content of the heat generating sheet 20. At the electrolyte content of 0.5% by weight or more, the oxidation reaction proceeds sufficiently in the resulting heat generating sheet 20. The water content in the heat generating sheet 20 for securing the electrolyte necessary to perform heat generating performance is not so high. As a result, the heat generating sheet 20 has a controlled heat capacity to achieve a sufficient temperature rise. At the electrolyte content of 30% by weight or less, precipitation of excess electrolyte is avoided to retain air permeability of the heat generating sheet 20. The water content in the heat generating sheet 20 necessary to provide a sufficient amount of the electrolyte for heat generation is secured to supply a sufficient amount of water to the oxidizable metal, etc. and to uniformly distribute the electrolyte throughout the heat generating sheet 20. As a result, excellent heat generating performance is obtained.

The water content of the heat generating sheet 20 is preferably 10% to 80% (by weight, hereinafter the same), more preferably 20% to 60%. At a water content of 10% or more, the water content necessary for continuing oxidation reaction is secured to allow the oxidation reaction to proceed sufficiently. Furthermore, water can be uniformly supplied throughout the heat generating sheet 20, leading to uniform heat generation. With a water content of 80% or less, the heat generating sheet 20 has a controlled heat capacity for the amount of heat generated, which leads to a sufficient rise in temperature. Besides, the air permeability of the heat generating sheet 20 is not impaired so that high heat generating performance and sufficient shape retention and mechanical strength are secured.

The thickness of the heat generating intermediate sheet 20 is preferably 0.08 to 1.2 mm, more preferably 0.1 to 0.6 mm. A heat generating intermediate sheet 20 having a thickness of 0.08 mm or more exhibits excellent heat generating performance and mechanical strength, satisfactory fixing capabilities for the oxidizable metal, the moisture-retaining agent, etc., and uniformity (stability) in thickness and composition. A break or the like of the sheet due to pinhole development, which leads to poor productivity and poor fabricability, hardly occurs. A sheet with a thickness of 1.2 mm or less has folding strength, hardly undergoes brittle fracture, and is soft to provide a comfortable fit when applied to a body. In addition, the time for papermaking and drying is short to provide good operationality. The heat generating performance becomes satisfactory. The sheet has excellent fabricability, hardly undergoing breakage or bending. The thickness of the heat generating intermediate sheet is obtained by taking measurements at five or more different points with Digimatic Indicator IDF-112 (measuring force: 1.28 N, available from Mitutoyo Corp.) and averaging the results.

The basis weight of the heat generating intermediate sheet 20 is preferably 10 to 1500 g/m$^2$, more preferably 50 to 900 g/m$^2$. Even in using, for example, an oxidizable metal, etc. having a high specific gravity, a stable sheet can be formed with a basis weight of 10 g/m$^2$ or more. A sheet weighing 1500 g/m$^2$ or less does not feel so heavy and gives comfort to a user and is produced with satisfactory productivity and operationality.

It is preferred for the heat generating intermediate sheet 20 to have a breaking length of 100 to 4000 m, more preferably 200 to 3000 m. With a breaking length of 100 m or longer, breaks and tears are prevented from occurring during production operations so that the sheet is formed in a stable manner; the resulting sheet is fabricated in a stable manner for the same reason; and the final product has moderate stiffness to give comfort to a user. A heat generating intermediate sheet 20 with a breaking length of 4000 m or less contains moderate amounts of the fibrous material and the binding component as the sheet-forming components and is therefore flexible and excellent in heat generating performance. The breaking length is measured as follows. A 15 mm wide and 150 mm long test piece cut out of a heat generating intermediate sheet 20 is subjected to a tensile test at an initial gauge length of 100 mm and a pulling speed of 20 mm/min in accordance with JIS P8113. A breaking length is calculated according to equation:

$$\text{Breaking length (m)} = (1/9.8) \times ((\text{tensile strength (N/m)}) \times 10^6 / (\text{basis weight of test piece (g/m}^2))$$

The temperature reached by the heat generating sheet 20 on heat generation is preferably 30° to 100° C., more preferably 35° to 90° C. This temperature is measured as follows. A 50 mm side square test piece cut out of a heat generating sheet 20 is sealed in between a water vapor permeable sheet and a water vapor impermeable sheet by bonding the periphery of the two sheets to make a bag. The water vapor permeable sheet has a water vapor permeability of 5 kg/(m$^2$·24 hr) as measured according to JIS Z0208. The bag containing the test piece is placed with the water vapor permeable sheet side up in a 4.2-liter closed chamber having a relative humidity of 1% or lower while feeding 5.0 l/min of dry air into the chamber to induce heat generating reaction. The temperature of the lower side of the bag measured with a thermocouple is the temperature reached by the sheet on heat generation. The temperature reachable by heat generation can freely be designed by the formulation of the components according to the purpose, that is, whether a steep temperature rise is desired or a long duration of heat generating reaction at a relatively low temperature is desired, and the like.

It is desirable for the heat generating sheet 20 to generate 1 to 100 mg/(cm$^2$·10 min), more preferably 1.0 to 50 mg/(cm$^2$·10 min), of water vapor per unit area (cm$^2$) for 10 minutes. The amount of water vapor generated is measured as follows.

A sheet is place in a 4.2-liter closed chamber having a relative humidity of 1% or less while feeding 5.0 l/min of dry air into the chamber and thus let to heat up. The sheet was set in the chamber so that water vapor generated may spread in the chamber. The humidity of the air discharged from the chamber is measured with a hygrometer, from which the amount of water vapor generated per unit time after the start of heat generation is calculated according to equation (1) shown below. The cumulative amount of water vapor generated for a period of 10 minutes is obtained and converted to a value per unit area. In the following equations, e stands for water vapor pressure (Pa); es, a saturated water vapor pressure (Pa; according to JIS Z8806); T, temperature (° C.; dry-bulb temperature); and s, sampling cycle (sec).

$$\text{Relative humidity } U(\% \text{ RH}) = (e/es) \times 100$$

$$\text{Absolute humidity } D(\text{g/m}^3) = (0.794 \times 10^{-2} \times e)/(1 + 0.00366T) = (0.794 \times 10^{-2} \times U \times es)/[100 \times (1 + 0.00366T)]$$

$$\text{Unit air volume } P(\text{liter}) = (2.1 \times s)/60$$

$$\text{Amount of water vapor per unit time } A(g) = (P \times D)/1000 \quad (1)$$

Similarly to the time required for reaching the maximum temperature of heat generation, the amount of water vapor produced can be freely designed by the formulation of the components according to the purpose, that is, whether a steep temperature rise is desired or a long duration of heat generating reaction at a relatively low temperature is desired, and the like.

As shown in FIG. 1, the holder 3 has its periphery sealed to form a joint 30 with a prescribed width to have the heat generating element 2 enclosed therein. In the first embodiment, the joint 30 is formed by heat sealing.

The holder 3 preferably has a water vapor permeability of 0.4 to 10 kg/(m$^2$·24 hr). A warming article having desired characteristics as well as an agreeable touch and conformity to a user's body can be designed by combining the water vapor permeability within the above recited range and the above-described capability of generating water vapor.

For instance, where the warming article is designed to slowly generate heat and water vapor with the onset of heat generating reaction of the heat generating element 2 after the warming article 1 is taken out of the package and to sustain the warming effect for a long duration with substantially no expansion and with excellent conformability to a body, a preferred water vapor permeability of the holder 3 ranges from 0.4 to 1.5 kg/(m$^2$·24 hr).

Where the warming article is designed to generate heat and water vapor immediately after it is taken out of the package, to start expanding without delay, and to provide an agreeable feel and a comfortable tight fit to the skin to make a user feel warmed and moisturized, a preferred water vapor permeability of the holder 3 is 1.5 to 10 kg/(m$^2$·24 hr), more preferably 2.0 to 8.0 kg/(m$^2$·24 hr).

Where the warming article is designed to generate heat and water vapor immediately after it is taken out of the package and to secure a tight fit to the skin to make a user feel warmed and moisturized without substantial expansion, it is preferred that the holder 3 have a water vapor permeability of 1.5 to 10 kg/(m$^2$·24 hr) and that the sheet have an air permeability of 30 sec/100 ml or less, more preferably 10 sec/100 ml or less.

The holder 3 may have air permeability partly or over the entire area thereof.

Figure 2:
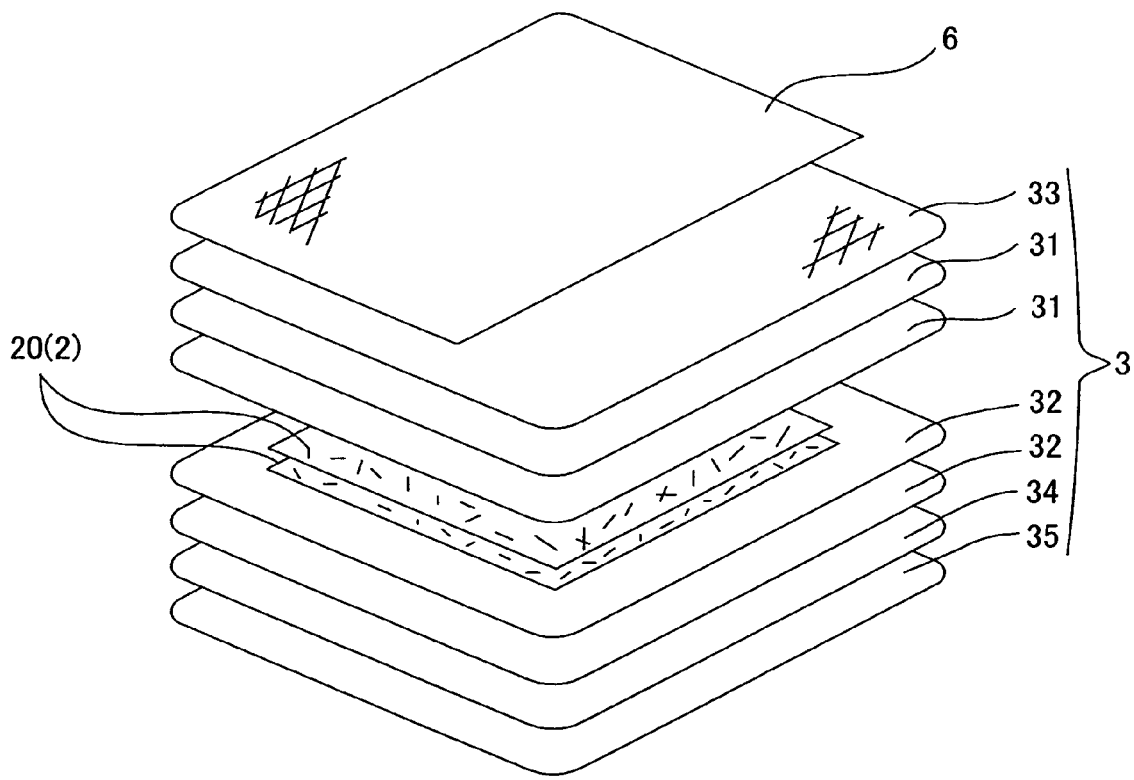
FIG. 2 is an exploded perspective schematically illustrating the warming article of the embodiment of FIG. 1

As shown in FIG. 2, the holder 3 of the warming article 1 according to the first embodiment has an air permeable sheet 31 and an air impermeable sheet 32 on the upper and the lower sides of the heat generating element 2, respectively. The warming article 1 of the present embodiment has the air permeable sheet 31 disposed on the side of the receiving part 5 of the heat generating element 2 so that water vapor may spread in the receiving part 5. By this design, the warming article 1 exerts a moisturizing function in the receiving part 5 as well as the heating function. When the heat and water vapor generating mechanism is combined with any functional agent as hereinafter described, this design enhances penetration of the functional agent.

The holder 3 of the warming article 1 according to the first embodiment has a three-layer structure on the upper side and a four-layer structure on the lower side of the heat generating element 2. The upper three-layer structure is composed of two air permeable sheets 31 and a surfacing member 33 disposed on the upper side of the air permeable sheets 31. The lower four-layer structure is composed of two air impermeable sheets 32 and a decorative member 34 and a surfacing member 35 disposed underneath the air impermeable sheets 32.

The water vapor permeability and air permeability of the air permeable sheet 31 are selected in accordance with the permeability to moisture and air required of the holder 3.

The air permeable sheet 31 preferably has a weight of 10 to 200 g/m$^2$, more preferably 20 to 100 g/m$^2$. The air permeable sheet 31 whose weight is in that range is thin and flexible, feels very pleasant, and does not impair the softness of the heat generating element.

The air permeable sheet 31 includes a mechanically perforated sheet of a resin, such as polyolefin (e.g., polyethylene or polypropylene), polyester, polyamide, polyurethane, polystyrene or an ethylene-vinyl acetate copolymer; a porous sheet obtained by stretching a sheet of the above-recited resin containing an inorganic filler (e.g., titanium oxide) to make pores by phase separation; and an open-cell sheet formed by foam molding. Woven or nonwoven fabrics made of synthetic pulp (e.g., polyolefin), wood pulp, non-wood pulp, semi-synthetic fibers (e.g., rayon and cellulose acetate), vinylon fiber, polyester fiber, etc., synthetic paper, and paper are also useful. While the air permeable sheet 31 may be used singularly, a plurality of the air-permeable sheets 31 may be stacked to hide the color of the heat generating sheets and to prevent fallen-off particles from precipitating on the surface.

The air impermeable sheet 32 can be of any material as long as it is impermeable to air. The air impermeable sheet 32 preferably has a water vapor permeability of 10 g/(m$^2$·24 hr) or less, more preferably 1.0 g/(m$^2$·24 hr) or less. The water vapor permeability of the air impermeable sheet 32 falling within that range, the water vapor is released only from the side of the air permeable sheet 31, and the side of the air impermeable sheet 32 preferentially supplies only heat.

The air impermeable sheet 32 preferably has a basis weight of 10 to 200 g/m$^2$, more preferably 20 to 100 g/m$^2$. Within this range of basis weight, the air impermeable sheet 32 is thin and flexible, feels very pleasant, and does not impair the softness of the heat generating element.

Materials of the air impermeable sheet 32 include synthetic resins such as polyolefin (e.g., polyethylene and polypropylene), polyester, polyamide, polyurethane, polystyrene, nylon, polyvinylidene chloride, and an ethylene-vinyl acetate copolymer etc. Where the air impermeable sheet 32 is required to hide the heat generating element from the sight, a sheet made of the above-recited resin having an inorganic filler (e.g., titanium oxide etc.) incorporated therein is used. While the warming article 1 of the present embodiment has two air impermeable sheets 32, only one sheet will do, or more than two sheets may be stacked.

The warming article 1 has a surfacing member 33 on the surface of the air permeable sheet 31 (i.e., the upper side of the warming article 1) and a surfacing member 35 on the surface of the impermeable sheet 32 (i.e., the lower side of the warming article 1). The surfacing member 35 not only give an agreeable feeling to the skin when the user put his or her hand in the receiving part 5 but is effective in relaxing heat conduction to give a user a mildly warmed feeling. It is possible to apply a chemical ingredient such as a skin cleaner or a furniture or hard surface cleaner, a medicinal ingredient such as a skin moisturizing agent or a line smoother, a heat-soluble gel or sol, a heat-released deodorant, and so forth to the surfacing member to provide the warming article 1 with various effects/efficacies.

The surfacing members 33 and 35 can be of any material having a good hand and flexibility. The thickness of the surfacing members is preferably 0.1 to 2.0 mm, more preferably 0.2 to 1.0 mm. Within that thickness range, the surfacing members relax the heat of the heat generating element to give a mild warm feel.

The basis weight of the surfacing members 33 and 35 preferably ranges from 5.0 to 200.0 g/m$^2$, more preferably 10.0 to 100.0 g/m$^2$. The surfacing member with a basis weight less than 5.0 g/m$^2$ is liable to break due to insufficient strength. The surfacing member with a basis weight more than 200.0 g/m$^2$ tends to feel rough or act as a heat insulator hindering heat conduction.

The surfacing members 33 and 35 can be formed of woven or nonwoven fabric of synthetic fibers, such as polyolefin (e.g., polyethylene or polypropylene), polyester (polyethylene terephthalate), polyamide, polyurethane, polystyrene, and ethylene-vinyl acetate copolymers, plant fibers, such as cotton and hemp, animal fibers, such as wool and silk, regenerated fibers, such as rayon and cuprammonium rayon, or semi-synthetic fibers, such as cellulose acetate; Japan paper; paper; synthetic paper; woven fabrics (e.g., woolen fabric); leather; and the like. Two or more surfacing members 33 or 35 may be used as stacked.

The warming article 1 has a decorative member 34 on the surface of (underneath) the air impermeable sheets 32. Any air impermeable sheet that serves a decorative purpose can be used as a decorative member 34. It is preferred for the decorative member 34 to have water vapor permeability of 10 g/(m$^2$·24 hr) or less, more preferably 1.0 g/(m$^2$·24 hr) or less. The water vapor permeability of the decorative member 34 falling within this range, the direction of water vapor's release can be controlled. That is, oxygen is supplied from the side of the air permeable sheets 31, and water vapor generated is released only from the air permeable sheet side while preventing water vapor dissipation from the side of the air impermeable sheets 32.

The decorative member 34 preferably has a basis weight of 10 to 200 g/m$^2$, more preferably 20 to 200 g/m$^2$. Within that range of basis weight, the decorative member 34 exhibits improved capability of hiding the heat generating element while retaining softness and flexibility of the warming article.

The decorative member 34 includes sheets made of synthetic resins, such as polyolefin (e.g., polyethylene or polypropylene), polyester, polyamide, polyurethane, polystyrene, nylon, polyvinylidene chloride, and ethylene-vinyl acetate copolymers etc. Where heat generating element hiding properties are demanded, in particular, a sheet of the above-recited resin having an inorganic filler (e.g., titanium oxide) etc. incorporated therein is used. Two or more decorative members 34 may be used as stacked.

The above-described members stacked in the described order are heat sealed at their periphery to make the holder 3, in which the heat generating element 2 (the heat generating sheets 20) is enclosed.

The heat generating main body 4 preferably has a thickness of 0.1 to 3.0 mm, more preferably 0.3 to 2.0 mm, and a basis weight of 100 to 9000 g/m$^2$, more preferably 200 to 4500 g/m$^2$, so as to provide a warming article that is thin, flexible, and conformable to a part of a body.

The receiving part-forming member 6 is heat sealed to the heat generating main body 4 along a continuous joint in such a configuration as to make an insertion opening 50. The joint may be discontinuous at an arbitrary interval to facilitate oxygen supply.

In the present embodiment, the receiving part-forming member 6 is formed of the same surfacing material as the surfacing member 33. Where the molded sheet is designed to not only heat up but expand, a mild pressure feeling is created in the inside of the receiving part by using, as the receiving part-forming member 6, the same surfacing material as the surfacing member 33. Depending on the intended use of the warming article, the receiving part-forming member 6 may be formed of other materials, such as the above-mentioned air permeable sheet, air permeable sheet or decorative member or a composite sheet composed of such a sheet and the above-mentioned surfacing material.

The warming article 1 is produced by, for example, disposing heat generating sheets 20, which are prepared as described below, at a prescribed position between upper and lower sheets making up the holder 3, fixing the periphery, or the entire area, of the heat generating sheets 20 by heat sealing or with a binder, bonding the periphery of all the upper and lower sheets to enclose the heat generating sheet 20 therebetween, cutting the laminate into a prescribed shape to form a heat generating main body 4, and bonding the receiving part-forming member 6 to the heat generating main body 4. The receiving part-forming member 6 may be bonded simultaneously with making the heat generating main body 4.

Production of the heat generating sheet 20 starts with preparation of a raw material composition (slurry) containing the oxidizable metal, the moisture-retaining agent, the fibrous material, and water.

A flocculant is preferably added to the raw material composition.

The flocculant includes inorganic ones, such as metal salts, e.g., ammonium sulfate, polyaluminum chloride, ferric chloride, polyferric sulfate, and ferrous sulfate; polymeric ones, such as polyacrylamides, sodium polyacrylates, Mannich base-modified polyacrylamide, aminoalkyl poly(meth)acrylates, sodium carboxymethyl celluloses, chitosans, starches, and polyamide-epichlorohydrins; organic flocculants, such as dimethyldiallylammonium chloride type or ethyleneimine type alkylene dichloride-polyalkylenepolyamine condensates, and dicyandiamide-formalin condensates; clay minerals, such as montmorillonite and bentonite etc.; silicon dioxide and its hydrates, such as colloidal silica; and hydrous magnesium silicate, such as talc etc. Preferred of these flocculants are combinations of an anionic agent and a cationic agent from the standpoint of sheet surface properties, formation, molding properties, properties of fixing the oxidizable metal, the moisture-retaining agent, etc., and sheet strength. Suitable combinations include a combination of colloidal silica or bentonite (anionic) and starch or polyacrylamide (cationic) and a combination of sodium carboxymethyl cellulose (anionic) and a polyamide-epichlorohydrin resin (cationic). In addition to these combinations, the above-recited flocculants can be used either individually or in combination of two or more thereof.

The flocculant is preferably added in an amount of 0.01% to 5% by weight, more preferably 0.05% to 1% by weight, based on the total solids content of the raw material composition. That the amount of the flocculant falls within the above range offers the following effects and advantages. A substantial flocculating effect is produced so that the components such as the oxidizable metal and the moisture-retaining agent are prevented from falling off in the step of papermaking. The raw material composition has a uniform composition to give a molded sheet with a uniform thickness and a uniform composition. The flocculant does not cause troubles affecting the productivity, such as the molded sheet sticking to drying rolls, breaking or scorching during the step of drying. The potential balance of the raw material composition is maintained to minimize fall-off of the above components into white water during papermaking. Oxidation is prevented from proceeding in the molded sheet thereby securing storage stability of the sheet in deoxidization characteristics, strength, and the like.

The concentration of the raw material composition preferably ranges 0.05% to 10% by weight, more preferably 0.1% to 2% by weight. Within that concentration range, a large quantity of water is not needed, and much time is not required for papermaking. Furthermore, the raw material composition can be a uniform dispersion to provide a molded sheet with good surface properties and a uniform thickness.

The raw material composition is formed into a molded sheet (heat generating intermediate sheet) by papermaking techniques.

Papermaking techniques for making the molded sheet include continuous papermaking by use of a cylinder paper machine, a foundrinier paper machine, a short-wire paper machine, a twin-wire paper machine, etc.; and batch papermaking such as standard sheet papermaking. A multilayer molded sheet may be obtained by using the above-described raw material composition and a composition having a different formulation. A multilayer molded sheet may also be obtained by laminating molded sheets separately prepared from the raw material composition or laminating a molded sheet prepared from the raw material composition and a molded sheet prepared from a composition having a different formulation.

The molded sheet is dewatered preferably to a water content of 70% or less (by weight, hereinafter the same), more preferably 60% or less, for assuring shape retention and mechanical strength after papermaking. Dewatering of the molded sheet after papermaking is carried out by, for example, suction, application of pressurized air or pressing with a pressure roll or a pressure plate.

The dewatered sheet, which contains the oxidizable metal capable of exothermic reaction in an ordinary atmosphere, is then subjected to positive drying to remove the water content. Removal of the water content provides a molded sheet that is inhibited from inducing oxidation of the oxidizable metal during the subsequent fabrication steps and has excellent long-term storage stability. Drying of the sheet is preferably carried out after the papermaking and before addition of an electrolytic solution containing the aforementioned electrolyte so that the oxidizable metal may be firmly fixed and held by the fibrous material and be prevented from falling off and that improvement in mechanical strength by addition of a heat fusible component or a thermal crosslinking component may be expected.

The molded sheet is preferably dried by heating. The heating temperature is preferably 60° to 300° C., more preferably 80° to 250° C. The heat drying temperature being in that range offers the following advantages. The drying time is moderate such that oxidation of the oxidizable metal, which proceeds with drying, is suppressed to retain the heat generating performance of the heat generating sheet. Accelerated oxidation of the oxidizable metal in the upper and lower skin layers of the heat generating sheet, which results in color change to pale brown, is avoided. Deterioration in performance of the moisture-retaining agent, etc. is not invited so that the heat generating performance of the heat generating sheet is maintained satisfactory. Abrupt water vaporization inside the molded sheet, which can destroy the sheet structure, is avoided.

The water content of the molded sheet after drying (i.e., the heat generating intermediate sheet) is preferably 20% or less, more preferably 10% or less. Where the water content is 20% or less, the resulting sheet has excellent long-term storage stability. For example, when the sheet is stored in a roll form, migration of excess water in the radial direction of the roll does not occur so that the heat generating performance and mechanical strength of the sheet will not change.

The method of drying the molded sheet is selected appropriately depending on the sheet thickness, the treatment given to the sheet before drying, the water contents before and after the drying, and the like. Useful drying methods include contact with a heating structure (heat generating element), application of heated air or water vapor (superheated water vapor), vacuum drying, microwave heating, electric current heating and the like. The drying may be carried out simultaneously with the above-described dewatering.

Shaping of the molded sheet (i.e., dewatering and drying) is preferably conducted in an inert gas atmosphere. Nevertheless, because the molded sheet is free from an electrolyte acting as an oxidation promoter, the shaping may be performed in an ordinary air atmosphere if desired, which enables simplification of equipment. Where necessary, the dried sheet is fabricated by craping, slitting, trimming or any other processings for shaping or forming etc. Thin and yet tearproof, the resulting molded sheet can be taken up in a roll. The molded sheet or a plurality of the molded sheets may be pressed either alone or as laminated with other film or sheet (e.g., paper, woven fabric, nonwoven fabric or plastic film). The plurality of the sheets and optionally the other film or sheet may be united into an integral sheet, given uneven patterns or perforated by pressing, embossing or needle punching. In order to facilitate laminating by heat sealing, a thermoplastic resin component or a hot-water-soluble component may be incorporated into the raw material composition.

The electrolyte is then incorporated into the molded sheet. The step of incorporating the electrolyte is preferably carried out in an inert gas atmosphere such as nitrogen or argon. Where the electrolyte is incorporated by impregnation with an electrolytic solution, the impregnating step may be conducted in an ordinary air atmosphere because oxidation that may proceed immediately after the impregnation is mild.

The electrolyte to be incorporated into the molded sheet is the same as used in the heat generating sheet.

The method of incorporating the electrolyte into the molded sheet is selected appropriately according to the treatment given to the sheet after papermaking, the water content and the form of the sheet, and the like. For example, the electrolyte can be incorporated by impregnating the molded sheet with an electrolytic solution having a prescribed electrolyte concentration or adding a powdered electrolyte having a prescribed particle size directly to the molded sheet. Impregnation is preferred for achieving uniform distribution of the electrolyte and simultaneously controlling the water content of the resulting sheet.

When the electrolyte is incorporated into the molded sheet by impregnation with an electrolytic solution, the manner of impregnation is chosen according to the form (e.g., thickness) and the water content of the sheet, and the like. Impregnation methods include spraying, syringing into part of the sheet (the injected electrolytic solution penetrates throughout the sheet by capillarity of the fibrous material), coating with a brush, etc., soaking in the electrolytic solution, gravure coating, reverse coating, doctor blade coating, and so forth. Spraying is preferred for uniform distribution, ease of operation, and relatively low cost of equipment. Where the finished product has a complicated shape or layer structure, syringing is preferred for productivity, process flexibility (the final finishing process can be done in a separate step), and simplicity of equipment. It is possible to conduct syringing after the molded sheet is enclosed in the holder.

Where necessary, the water content of the molded sheet containing the electrolyte is adjusted to provide a stabilized heat generating sheet. If desired, the heat generating sheet thus prepared can be fabricated by trimming into a prescribed size or stacked one on top of another.

Figure 3:
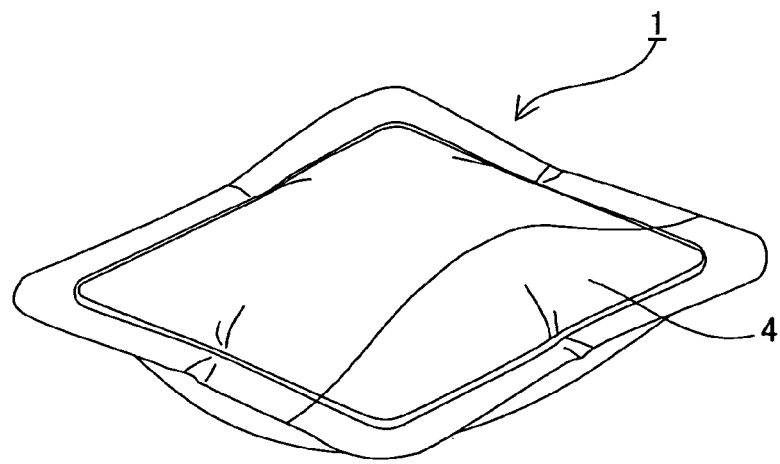
FIG. 3 is a schematic perspective of the warming article of the embodiment of FIG. 1, with the heat generating main body expanded.
Figure 4:
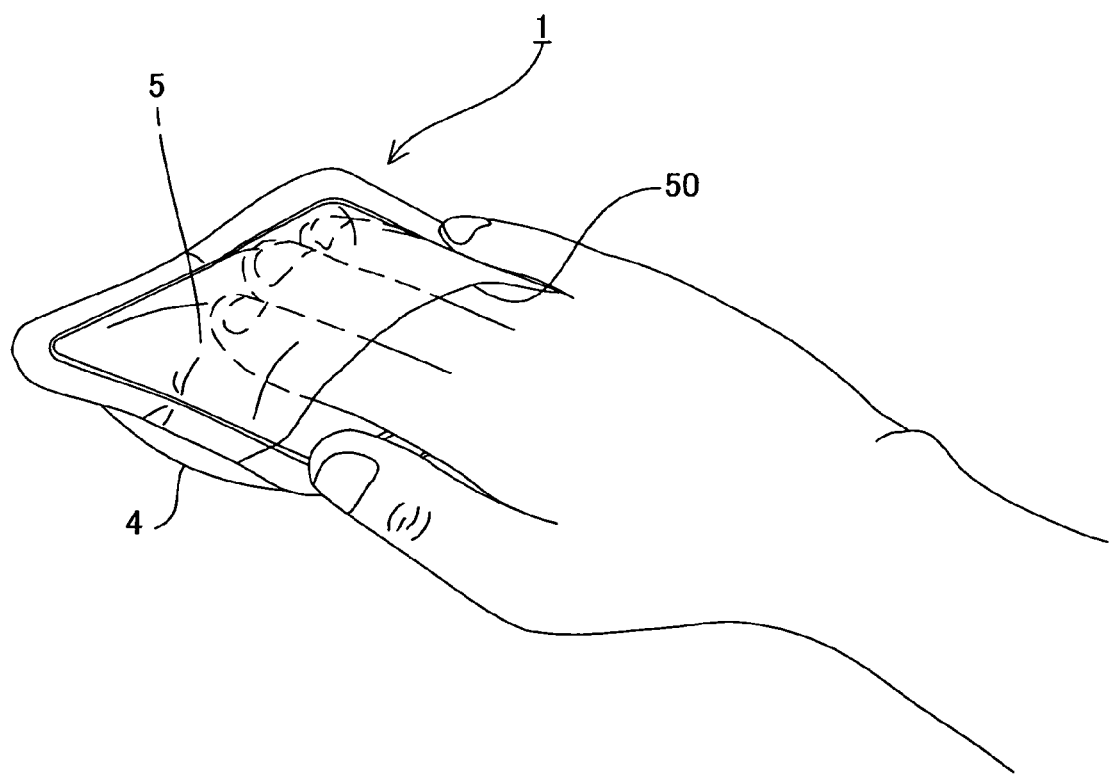
FIG. 4 is a perspective schematically illustrating the warming article of the embodiment of FIG. 1 while in use.

The warming article 1 of the first embodiment is supplied as sealed in an air impermeable package until use. On taking the warming article 1 from the package, exothermic reaction of the heat generating element 2 takes place to generate water vapor whereby the heat generating main body 4 expands as illustrated in FIG. 3. A hand is inserted through the opening 50 into the receiving part 5 as illustrated in FIG. 4. The receiving part 5 is warmed by the heat generated by the oxidation of the oxidizable metal and, at the same time, humidified by the water vapor generated by the heat. The warming article 1 exerts moderate tightness in the receiving part 5 to provide an agreeable comfort to wear. The warming article 1 may be used with its side releasing no water vapor applied to an object to be warmed to give only heat to the object.

Where the warming article 1 of the first embodiment is configured to expand the heat generating main body 4 by the water vapor accompanying heat generation of the heat generating element 2, it provides a comfort to wear with an agreeable touch and moderate tightness when a hand is put into the receiving part. The warming article 1 is capable of not only warming the hand with the heat generated by oxidation of the oxidizable metal but moisturizing the hand by the water vapor generated by the heat and spread in the receiving part 5. Since the heat generating element 2 is composed of the heat generating sheets 20, the warming article 1 is thin and conveniently portable. In addition, the warming article 1 keeps flexible from before use through to after the completion of the exothermic reaction. From this aspect, too, the warming article 1 is agreeable to wear.

The warming article 1 enjoys a diversity of uses by taking advantage of the warming and moisturizing functions and the tight fit in the receiving part 5 combined with various functional agents. For instance, a functional agent may previously be applied to the part of a body to be warmed, or an inner layer of the receiving part may be impregnated with a functional agent, and the part of the body is inserted in the receiving part. In this case, the functional agent exhibits high penetrability through the skin. When combined with hot packs or cataplasm, the warming article 1 is also useful for skin care (for moisturizing, wrinkle reduction, etc.) or health care (for relief of pain, etc.). Since the warming article 1 is capable of moisturizing as well as warming while providing a moderately tight fit in the receiving part, combination with such a functional agent achieves high penetration of the functional agent into the skin. In some applications, particularly where the warming article is directly applied to a body to conduct warming and moisturizing, it is desirable for the warming article to come into planar contact without expansion. Accordingly, the expanding function of the warming article can be designed freely so that the effect-efficacy of the commercial product may be fully displayed.

Figure 5A:
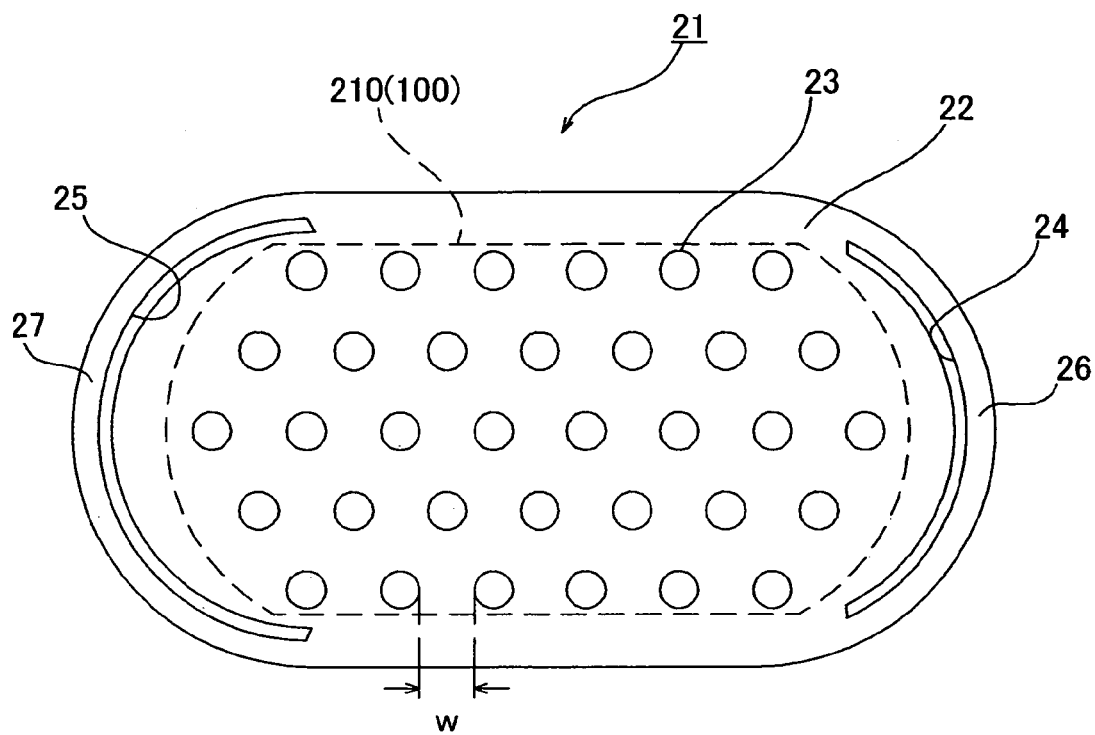
Figure 5B:
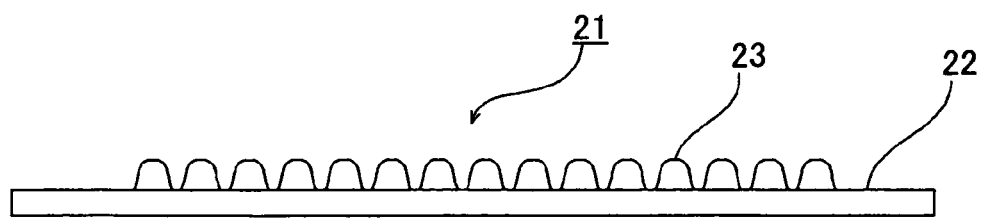
Figure 6A:
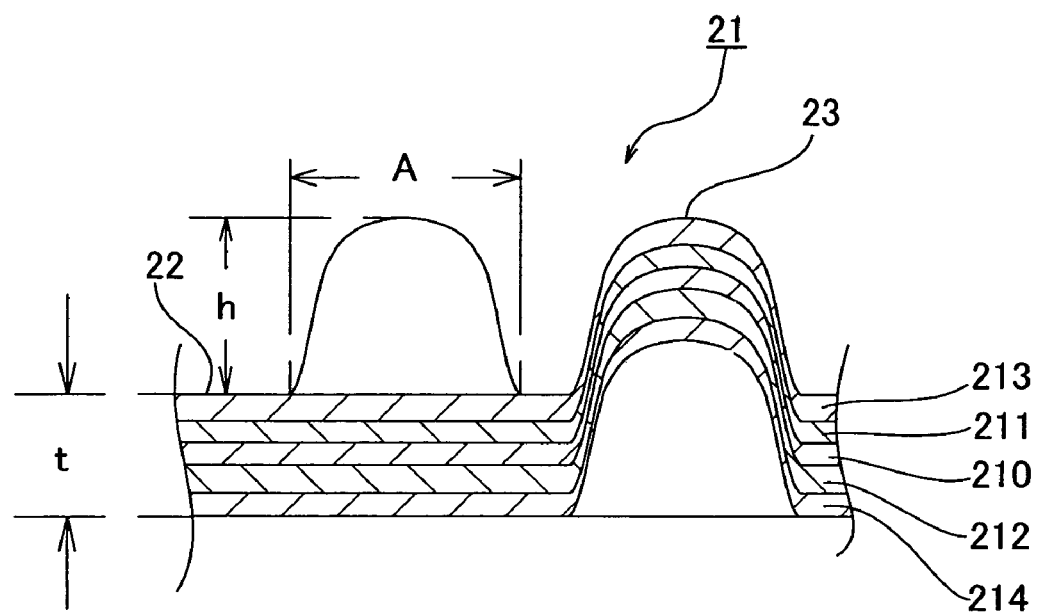
Figure 6B:
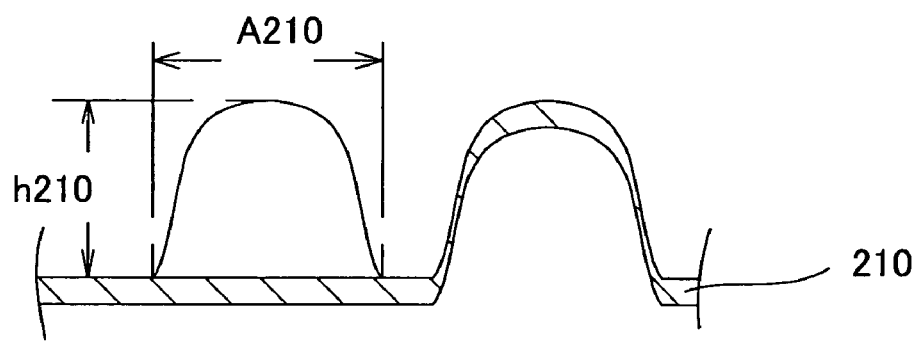
Figure 7:
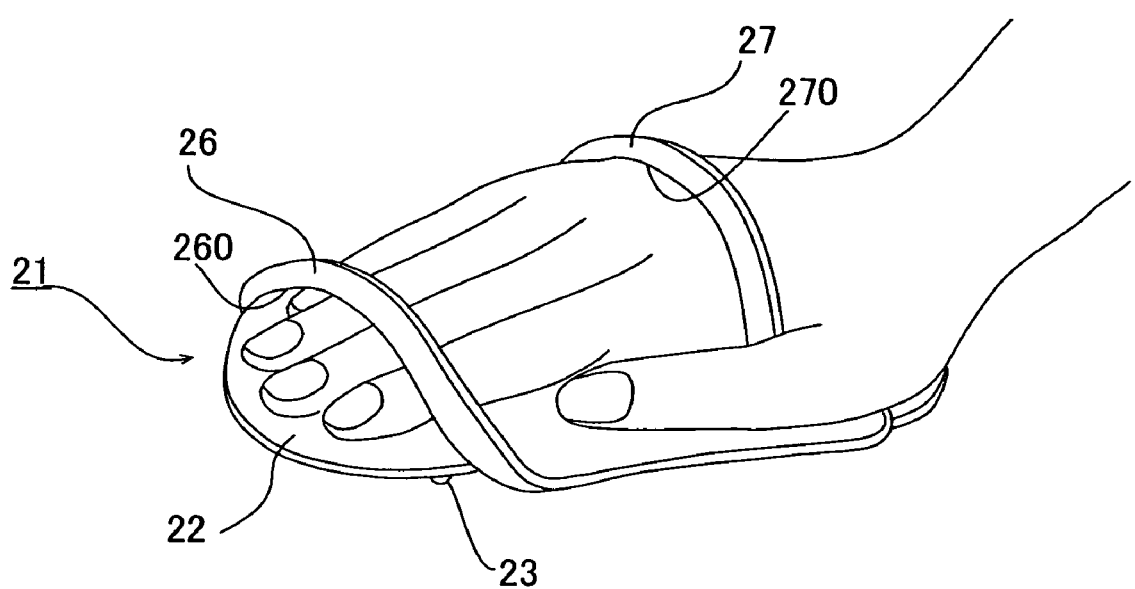
FIG. 7 is a perspective schematically illustrating the warming article of the embodiment of FIGS. 5(a) and 5(b) while in use.

FIGS. 5 through 7 represent an embodiment wherein the warming article of the present invention is applied to a brush type warming article. In the figures, numerical reference 21 indicates the warming article.

As illustrated in FIG. 5, the warming article 21 has a flat base 22 having an elongated circular outline in its plan view. The base 22 has a large number of three-dimensional projections 23. The base 22 has slits 24 and 25 cut along the arch on each end thereof.

As illustrated in FIG. 5, the warming article 21 has a heat generating, shaped article 100, which is obtained by three-dimensionally shaping a molded sheet 210. The molded sheet 210 is prepared by papermaking and contains an oxidizable metal, a moisture-retaining agent, and a fibrous material (a molded sheet 210 which does not contain an electrolyte will be called a heat generating intermediate sheet 210, and a molded sheet 210 containing an electrolyte (hereinafter described) and water will be called a heat generating sheet 210). The heat generating shaped article 100 is the heat generating sheet having been shaped by heat pressing. The heat generating sheet is disposed between an air permeable sheet 211 and an air impermeable sheet 212 and heat-pressed together with the air permeable sheet 211, the air impermeable sheet 212, and nonwoven fabrics 213 and 214 into a unitary article.

While dry, the heat generating intermediate sheet 210 preferably has at least 50% by weight, more preferably 70% by weight or more, even more preferably 80% by weight or more, of components other than the fibrous material. Where the proportion of the components other than the fibrous material is 50% by weight or more, the temperature can rise to a degree that is felt hot on touching with fingers, etc. While it is desirable that the proportion of the components other than the fibrous material be increased as much as possible, the upper limit would be 98% by weight for securing sufficient strength to maintain fabricability of the heat generating intermediate sheet 210. The proportion of the components other than the fibrous material is measured as follows.

The proportion of the components other than the fibrous material in the heat generating intermediate sheet 210 is obtained in the same manner as with the heat generating intermediate sheet 20 of the first embodiment.

The oxidizable metal can be of any kind that is commonly employed in this type of heat generating molded articles with no particular limitation. The same oxidizable metal as used in the heat generating intermediate sheet 20 of the first embodiment is preferably used.

The proportion of the oxidizable metal in the heat generating intermediate sheet 210 is preferably the same as in the heat generating intermediate sheet 20 of the first embodiment.

The moisture-retaining agent can be of any kind that has been commonly employed in heat generating molded articles with no particular limitation. The same moisture-retaining agent as used in the heat generating intermediate sheet 20 of the first embodiment is preferably used.

The amount of the moisture-retaining agent in the heat generating intermediate sheet 210 is preferably the same as in the heat generating intermediate sheet 20 of the first embodiment.

The fibrous material is preferably the same as used in the heat generating intermediate sheet 20 of the first embodiment.

The amount of the fibrous material in the heat generating intermediate sheet 210 is preferably the same as in the heat generating intermediate sheet 20 of the first embodiment.

The heat generating intermediate sheet 210 may contain the same flocculant as used in the heat generating intermediate sheet 20 of the first embodiment.

Similarly to the heat generating intermediate sheet 20 of the first embodiment, the heat generating sheet 210 may contain, according to necessity, additives commonly used in papermaking, such as sizes, colorants, strengthening agents, yield improvers, loading materials, thickeners, pH control agents, and bulking agents, with no particular limitation. The amounts of the additives to be added can be selected appropriately according to the kinds.

The thickness of the heat generating intermediate sheet 210 is preferably the same as of the heat generating intermediate sheet 20 of the first embodiment.

The basis weight of the heat generating intermediate sheet 210 is preferably the same as of the heat generating intermediate sheet 20 of the first embodiment.

The breaking length of the heat generating intermediate sheet 210 is preferably the same as of the heat generating intermediate sheet 20 of the first embodiment.

The electrolyte to be contained in the heat generating sheet 210 can be of any kind that has been commonly employed in this type of heat generating molded articles with no particular limitation. The same electrolyte as used in the heat generating intermediate sheet 20 of the first embodiment is preferably used.

The amount of the electrolyte in the heat generating sheet 210 is preferably the same as in the heat generating intermediate sheet 20 of the first embodiment. The amount is preferably 0.5% to 30% by weight, more preferably 1% to 25% by weight, based on the water content of the heat generating sheet 210. At the electrolyte content of 0.5% by weight or more, the oxidation reaction proceeds sufficiently in the resulting heat generating sheet 210. Furthermore, since the water content is minimized to secure a necessary amount of the electrolyte for heat generation, a reduction in temperature rise is minimized. At the electrolyte content of 30% by weight or less, precipitation of excess electrolyte is avoided to retain air permeability of the heat generating sheet 210. The water content in the heat generating sheet 210 necessary to provide a sufficient amount of the electrolyte for heat generation is secured to supply a sufficient amount of water to the oxidizable metal, etc. and to uniformly distribute the electrolyte throughout the heat generating sheet 210. As a result, excellent heat generating performance is obtained.

The heat generating sheet 210 preferably has a maximum stress of 0.3 to 5 MPa, preferably 0.6 to 4 MPa, more preferably 1.0 to 3 MPa. The heat generating sheet 210 having a maximum stress of 0.3 MPa or more hardly breaks at the projections (hereinafter explained) and the foot of the projections and therefore exhibits uniform heat generating performance. Furthermore, the oxidizable metal, the moisture-retaining agent or like components are prevented from falling off and contaminating the object in contact during use. As long as the maximum stress is 5 MPa or less, a certain proportion of the components other than the fibrous material is secured in the heat generating sheet to assure sufficient heat and water vapor generation thereby providing pronounced commodity attractiveness.

The heat generating sheet 210 has a breaking elongation of 2.0% to 10%, preferably 2.5% to 7%, more preferably 3.0% to 5%. The heat generating sheet 210 having a breaking elongation of 2.0% or more hardly breaks at the projections (hereinafter explained) and the foot of the projections and therefore exhibits uniform heat generating performance. Furthermore, the contamination problem due to fall-off of the oxidizable metal, the moisture-retaining agent, etc. hardly occurs. As long as the breaking elongation is 10% or less, a certain proportion of the components other than the fibrous material sufficient heat and water vapor generation thereby providing pronounced commodity attractiveness.

The heat generating intermediate sheet 210 has a maximum stress of 0.5 to 15 MPa, preferably 1.0 to 12 MPa, more preferably 1.2 to 10 MPa, while dry. With the maximum stress of 0.5 MPa or more, the projections (hereinafter described) and their foot are prevented from breaking etc. during press forming so that uniform heat generating performance can be obtained. Furthermore, the oxidizable metal, the moisture-retaining agent, and the like are prevented from falling off and entering the surfacing member. With the maximum stress of 15 MPa or less, the heat generating intermediate sheet is prevented from wrinkling or developing a large crack, thereby providing a commercially attractive product having a good appearance with a uniform thickness. The maximum stress while dry was measured as follows. A resulting heat generating intermediate sheet was dried, and a test piece measuring 15 mm wide and 150 mm long was cut out. The test piece was set on a tensile tester (RTA-500 from Orientec) at an initial gauge length of 100 mm and pulled at a pulling speed of 20 mm/min in accordance with JIS P8113.

The heat generating intermediate sheet 210 has a breaking elongation of 0.8% to 5%, preferably 1% to 4%, more preferably 1.5% to 3%, while dry. With the breaking elongation of 0.8% or more, the projections (hereinafter described) hardly break, and prevent fall-off of the oxidizable metal, the moisture-retaining agent, or the like. With the breaking elongation of 5% or less, uniform projections can be formed, and the heat generating intermediate sheet is prevented from having a non-uniform thickness and developing wrinkles. The breaking elongation is measured in the same manner as for the maximum stress.

The heat generating sheet 210 preferably has the same water content as recited with respect to the heat generating sheet 20 of the first embodiment.

The temperature reached by the heat generation of the heat generating sheet 210 is preferably the same as that of the heat generating sheet 20 of the first embodiment.

The amount of water vapor generated from the heat generating sheet 210 per unit area for 10 minutes is preferably the same as that of the heat generating sheet 20 of the first embodiment. The amount of water vapor generated is measured in the same manner as described for the heat generating sheet 20 of the first embodiment.

The amount of water vapor generated from the heat generating sheet 210 as well as the time required for reaching the maximum temperature can freely be designed by the aforementioned formulation of the components according to the end use of the product, for example, whether abrupt heat generation is desired or a long duration of heat generation at a relatively low temperature is desired.

Any air permeable sheet can be used as the air permeable sheet 211. The air permeable sheet 211 preferably has a water vapor permeability of 100 to 10000 $g/(m^2 \cdot 24\ hr)$, more preferably 1000 to 8000 $g/(m^2 \cdot 24\ hr)$. With the water vapor permeability being in that range, the warming article rapidly generates heat and water vapor immediately after it is taken out of the package so that a user may feel warmed and moisturized without wait. Furthermore, a functional agent, when used in combination, will exhibit enhanced penetrability. The air permeable sheet 211 may have air permeability all over the entire area or partly.

The basis weight of the air permeable sheet 211 is preferably the same as that of the air permeable sheet 31 used in the first embodiment.

The air permeable sheet 211 is preferably made of the same material as of the air permeable sheet 31 used in the first embodiment.

Any air impermeable sheet can be used as the air impermeable sheet 212. The air impermeable sheet 212 preferably has the same water vapor permeability as that of the air impermeable sheet 32 of the first embodiment.

The basis weight of the air impermeable sheet 212 is preferably the same as that of the air impermeable sheet 32 of the first embodiment.

The air impermeable sheet 212 is preferably made of the same material as of the air impermeable sheet 32 used in the first embodiment.

The warming article 21 of the embodiment has the nonwoven fabric 213 disposed on the surface of the air permeable sheet 211. The nonwoven fabric 213 is not particularly limited in material and production process as long as it gives no adverse influences on the air permeability of the air permeable sheet 211, the heat generating performance of the warming article 21, functional agent retentivity, and utility (cleaning, wiping, massaging, brushing, etc.) and effect as a commodity. Materials of the nonwoven fabric 213 include synthetic fibers, natural fibers, and composite fibers thereof. Production processes include spun bonding, needle punching, hydroentanglement, melt blowing, flash spinning, air laying, through-air processing, and papermaking. Taking the functional agent retentivity into consideration, hydroentanglement is preferred for its applicability to fibers having high water and oil retentivity exemplified by rayon and cotton.

Taking functional agent retentivity and the above-described commodity's utility into consideration, the basis weight of the nonwoven fabric 213 is preferably 5 to 200 $g/m^2$, more preferably 10 to 100 $g/m^2$. With the basis weight of 5.0 $g/m^2$ or more, sufficient strength is secured, and the heat from the heat generating element is prevented from being transferred directly to the skin thereby lessening irritation. With the basis weight of 200 $g/m^2$ or less, the surfacing member sufficiently transfers the heat of the heat generating element to the skin.

The warming article 21 of the second embodiment has the nonwoven fabric 214 disposed on the surface of the air impermeable sheet 212. The nonwoven fabric 214 is not particularly limited in material and production process. Materials of the nonwoven fabric 214 include synthetic fibers, natural fibers, and composite fibers thereof. Production processes include spun bonding, needle punching, hydroentanglement, melt blowing, flash spinning, air laying, through-air processing, and papermaking. Through-air processing and air laying processing are preferred for providing nonwoven fabric with softness and flexibility. Hydroentanglement is preferred for its applicability to a wide range of fibers.

The basis weight of the nonwoven fabric 214 is not particularly limited. Taking softness and flexibility of the warming article into consideration, the basis weight is preferably 5 to 200 $g/m^2$, more preferably 10 to 100 $g/m^2$.

The warming article 21 preferably has a thickness (t) of 0.5 to 10 mm, more preferably 1 to 5 mm, at the base 22, taking the shape retention, convenience to use, and flexibility of the product into consideration.

The arrangement and the three-dimensional geometry of the projections 23 are decided appropriately according to the intended use, convenience to use, and the characteristics required of the product.

As illustrated in FIG. 5(a), the projections 23 are arranged at apices of regular triangles connected with edges shared. As illustrated in FIG. 6(a), each of the projections 23 is tapered to the top, and the top is rounded at a given curvature.

The projection 23 preferably has a height h (from the surface of the base 22) of 1 to 50 mm, more preferably 3 to 30 mm, taking into consideration brushing effects, ease for the projections to reach the surface of an object to be warmed, strength and the resultant pressing effect of the projections, and formability by press forming. For the same consideration, the projection 23 preferably has a diameter A (diameter at the foot) of 1 to 100 mm. From the same viewpoint, the projection 23 preferably has a radius curvature of 0.1 to 200 mm. From the same viewpoint, the distance w between adjacent projections (foot-to-foot distance, see FIG. 5) is preferably 0.5 to 50 mm. Understandably, the number of the projections 23 may be one for some applications.

As shown in FIG. 6(a), all the five layers inclusive of the heat generating sheet 210 are three-dimensionally shaped to form the individual projections 23 without breaks or cuts. The heat generating shaped article 100 obtained by three-dimensionally shaping the heat generating sheet 210 has a projection height h210 (from the flat basal part of the heat generating sheet) of 2 to 20 mm. The projection 23 of the heat generating shaped article 100 has a diameter A210 (diameter at the foot) of 2 to 20 mm. The curvature radius of the projection 23 is 0.5 to 10 mm. The distance between adjacent projections (foot-to-foot) is 1 to 20 mm.

The warming article 21 preferably reaches a temperature of 30° to 90° C., more preferably 35° to 60° C., at the surface of the projections 23. In that temperature range, the pressing effect by the projections 23 and the warming and moisturizing effects by the heat generating sheet 210 are produced synergistically. The warming article may be designed to generate water vapor only from the projections.

On use, arc-shaped strips 26 and 27 formed outboard of the slits 24 and 25 (see FIG. 5) are bent opposite to the projecting direction of the projections 23 to make receiving parts 260 and 270, through which a hand is inserted as illustrated in FIG. 7.

The warming article 21 is produced by, for example, preparing the heat generating sheet 210 as described below, stacking other members on the heat generating sheet 210 to make a multilayer structure having the above-described layer structure, and three-dimensionally shaping the structure.

Preparation of the heat generating sheet 210 starts with preparation of a raw material composition (slurry) containing the aforementioned oxidizable metal, moisture-retaining agent, and fibrous material and water.

The aforementioned flocculant is preferably added to the raw material composition.

It is preferable to use the same flocculants as used in the preparation of the heat generating sheet 20 of the first embodiment.

The amount of the flocculant to be added is preferably the same as used in the preparation of the heat generating sheet 20 of the first embodiment. It is preferred to use a sheet of the same material as used as the air permeable sheet 31.

The concentration of the raw material composition is preferably the same as in the preparation of the heat generating sheet 20 of the first embodiment.

The raw material composition is made into the above-described molded sheet (heat generating intermediate sheet) by papermaking.

Papermaking is preferably carried out in the same manner as for the heat generating intermediate sheet of the first embodiment.

The water content of the molded sheet is preferably the same as of the molded sheet of the first embodiment.

The molded sheet, which contains the oxidizable metal capable of exothermic reaction in an ordinary atmosphere, is then subjected to positive drying to remove the water content. Removal of the water content provides a molded sheet that is inhibited from inducing oxidation of the oxidizable metal during the subsequent fabrication steps and has excellent long-term storage stability. Drying of the sheet is preferably carried out after the papermaking and before addition of an electrolytic solution containing the aforementioned electrolyte so that the oxidizable metal may be firmly fixed and held by the fibrous material and be prevented from falling off and that mechanical strength improvement by addition of a heat fusible component or a thermal crosslinking component may be expected.

The heat fusible component includes high-density polyethylene, medium-density polyethylene, low-density polyethylene, polypropylene, polyester, polyvinylidene chloride, polyvinyl alcohol, polyvinyl acetate, and the copolymers.

The thermal crosslinking component includes phenol resins, epoxy resins, urea resins, furan resins, polyurethane resins, amino resins such as melamine, unsaturated polyester resins, and diallyl phthalate resins.

Drying of the molded sheet is preferably carried out by heating at the same temperature as for the molded sheet of the first embodiment.

The water content after the drying is preferably the same as that of the dried molded sheet of the first embodiment.

The method of drying the molded sheet is selected appropriately depending on the sheet thickness, the treatment given to the sheet before drying, the water contents before and after the drying, and the like. Useful drying methods include contact with a heating structure (heat generating element), application of heated air or water vapor (superheated water vapor), vacuum drying, microwave heating, electric current heating and the like. The drying may be carried out simultaneously with the above-described dewatering.

Shaping of the molded sheet (i.e., dewatering and drying) is preferably conducted in the same manner as in the first embodiment.

The air permeable sheet 211, the air impermeable sheet 212, the nonwoven fabrics 213 and 214 are superposed on the upper and the lower sides of the resulting molded sheet, and the resulting multilayer structure is placed in a press mold for three-dimensional shaping, and heat pressed in the mold to form the projections 23. There is thus obtained a three-dimensionally shaped, multilayered article.

The heat pressing temperature is preferably 80° to 200° C., more preferably 90° to 150° C. Within that temperature range, the molded sheet can be united with the surfacing sheets and the nonwoven fabrics uniformly without breaks.

The heat pressing pressure is preferably 0.1 to 20 MPa, more preferably 0.5 to 10 MPa. Within that pressure range, there is provided a tearproof warming article with shape retention at the projections and strength and uniformity of the projections fit for the intended commodity use.

The heat pressing time is preferably 0.5 to 60 seconds, more preferably 1 to 30 seconds. Heat pressing for that time allows for stable formation of the projections with high productivity.

The multilayer shaped article having the projections 23 is cut along a prescribed contour, and the slits 24 and 26 are cut. If necessary, the article is trimmed to a prescribed size.

An electrolytic solution is then incorporated into the molded sheet (heat generating intermediate sheet) of the heat-pressed, multilayer structure. A syringing method, in which the electrolytic solution is injected into part of the molded sheet by use of a syringe, etc. and penetrated throughout the molded sheet by capillarity of the fibrous material, is preferred in view of improved productivity even in the production of articles with a complicated shape or layer structure, process flexibility (the final finishing process can be done in a separate step), and simplicity of equipment. It is possible to conduct syringing after the electrolyte-free warming article is enclosed in a package.

The step of incorporating the electrolyte is preferably carried out in the same manner as for incorporating the electrolyte into the molded sheet in the first embodiment.

Where necessary, the water content of the molded sheet containing the electrolyte is adjusted to provide a stabilized warming article. The resulting warming article is packaged in an oxygen impermeable packaging material.

As illustrated, the warming article 21 of the second embodiment is a multilayer structure composed of the heat generating sheet 210, the air permeable sheet 211, the air impermeable sheet 212, and the nonwoven fabrics 213 and 214 and heat-pressed to form the projections 23 with good precision. The heat generating sheet 210 suffers from neither a tear nor a wrinkle as a result of heat pressing. Performing a warming and moisturizing function by the heat generating sheet 210 (the heat generating shaped article 100) and a pressing function (massaging function) by the projections 23, the warming article 21 is applicable to a diversity of uses. For example, the warming article 21 is suited for applications aiming at hair growth promotion, hair loss prevention, or bedhead styling by hot scalp massage, a slimming effect by massage on the arms, legs, hips, etc, or a depilatory effect.

The present invention is not construed as being limited to the foregoing embodiments, and it should be understood that various changes and modifications can be made therein without departing from the spirit and scope thereof.

For example, the warming article 1 of the first embodiment, which is designed to have air permeability only on the side of the holder 3 where the receiving part 5 is provided, may be designed to have air permeability only on the side where the receiving part is not provided. In this case, the air permeable side is faced to an object to be treated with or without contact to exert the moisturizing effect as well as the warming effect to the object. A warming article of this type is suitably combined with various functional preparations for, for example, cleaning, sterilization, slow wax release, scenting or deodorization, and useful in home care applications (cleaning or treatment of flooring, tatami, kitchen stoves and fans, etc.), air care applications to create a comfortable ambience, car care applications (cleaning and waxing), and facial and body skin care applications (cleansing, sterilizing, moisturizing, and make-up removal). When combined with a pack, the warming article provides a skin-care hot pack for moisturizing, eliminating darkness under the eye, wrinkles or skin dullness or slimming or an eye-care hot pack for improving eyesight. When combined with cataplasm, the warming article provides health-care hot cataplasm for alleviating pains in the neck, shoulders, feet, the lower back, etc. or period pains. The warming article is also useful for hair care applications in permanent waving, hair dyeing or hair growth promotion and for medical applications as combined with drugs such as athlete's foot remedy. Additionally, the warming article is useful as disposable bedding including comforters, blankets, and covers therefor; disposable mats or sheets including, cushions, lap rugs, ground sheets, and pet sheets; disposable horticultural sheets including frost-preventive sheets for bonsai and other plants; and packaging materials for foods, etc.

The warming article of the present invention can have the layer structure, inclusive of the heat generating element, holder, and receiving part-forming member, varied appropriately according to the intended use. For instance, the warming article of the first embodiment, which is designed to have air permeability on only one side of the heat generating main body to make water vapor be released from that side, may be designed to have water vapor spread from both sides, i.e., inside the receiving part and from the side with no receiving part.

The holder 3 of the first embodiment, which has a multilayer structure, may have a single layer structure as long as it exhibits air permeability required for inducing oxidation reaction and expansion of the heat generating main body and performs the function of preventing the heat generating element-constituent components from falling off.

While in the first embodiment, sealing of the holder and joining of the holder and the receiving part-forming member are achieved by heat sealing, other sealing and joining methods may be used, including adhesion with an adhesive or sewing.

The heating generating main body and the receiving part of the warming article of the present invention can be shaped in conformity to a part of a body to be inserted including not only a hand as in the first embodiment but a foot, an ear, etc. and thereby made fit for various applications. For example, a warming article the receiving part of which is designed to accommodate the head is used for hair care applications such as permanent waving, hair dyeing, and hair growth promotion. A warming article shaped as a face mask may have ear hooks formed so as to come into closer contact with the facial skin to give warmth and moisture to the face uniformly.

The receiving part of the warming article may be provided by partly joining the heat generating main body to itself instead of joining the receiving part-forming member 6 to the heat generating main body 4. In this case, the warming article may be designed to release water vapor only inside or outside or both inside and outside the receiving part.

While it is preferred for the warming article of the present invention to have the receiving part, the receiving part may be omitted for some applications.

The warming article 21 of the second embodiment, which is produced by stacking the molded sheet (heat generating intermediate sheet), the air permeable sheet, the air impermeable sheet, and the nonwoven fabrics and heat-pressing the resulting multilayer structure, may be produced by previously pressing only the molded sheet into a three-dimensional contour and then superposing the other members.

It is preferred for the heat generating shaped article and the warming article according to the present invention to contain an electrolytic solution of an electrolyte in the heat generating sheet 210 as in the warming article 21 of the second embodiment. Otherwise, the heat generating sheet may be supplied in the state freed of the electrolyte and given the electrolyte upon use. Where the sheet is free of an electrolyte, the production steps do not need to be conducted in an oxygen-free or low-oxygen atmosphere, which allows for simplification of the production steps per se and equipment for the production.

Unlike the process adopted in the second embodiment, the three-dimensionally shaped warming article may be produced by first incorporating the electrolyte into the molded sheet (heat generating intermediate sheet), superposing the air permeable sheet 211, the air impermeable sheet 212, and the nonwoven fabrics 213 and 214 on the molded sheet containing the electrolyte, and heat pressing the multilayer structure in a press mold to form the projections 23.

In addition to the method adopted in the second embodiment, the method of incorporating the electrolyte into the molded sheet (heat generating intermediate sheet) is selected appropriately according to the treatment given to the molded sheet after papermaking, the water content and the form of the sheet, and the like. For example, the electrolyte can be incorporated by impregnating the molded sheet with an electrolytic solution by use of a syringe as in the second embodiment or other impregnation methods described below or by adding a powdered electrolyte having a prescribed particle size directly to the molded sheet. Impregnation is preferred for achieving uniform distribution of the electrolyte and simultaneously controlling the water content of the resulting sheet.

When the electrolyte is incorporated into the molded sheet by impregnation with an electrolytic solution, the manner of impregnation is chosen according to the form (e.g., thickness) and the water content of the molded sheet, and the like. Impregnation methods include spraying, coating with a brush, and soaking as well as the aforementioned syringing.

The three-dimensional shape of the heat generating shaped article and the warming article according to the present invention is subject to variation depending on the use. For spot application of warmth and moisture, the heat generating shaped article or warming article can be shaped into masks, etc. with an easy-to-grasp three-dimensional shape. The heat generating shaped article or warming article may also be shaped into full face masks, eye masks, slippers or, for applications to foods, trays or cups.

The layer structure of the warming article of the present invention including the heat generating sheet, the air permeable sheet, and the air impermeable sheet can be altered according to the use. For example, while the warming article of the second embodiment is configured to have air permeability on only one side thereof to allow water vapor to be released from that side, the holder may be formed of two air permeable sheets joined together, whereby water vapor is allowed to be released from both sides of the heat generating sheet.

While in the second embodiment joining of the air permeable sheet and the air impermeable sheet is achieved by heat sealing accompanying heat pressing, other sealing and joining methods may be used, including adhesion with an adhesive, fusion cutting, and ultrasonic sealing.

The warming article of the present invention is useful in other applications than the use referred to with respect to the second embodiment. For example, it is combined with various functional preparations for cleaning, sterilization, slow wax release, scenting or deodorization to provide a hot brush suited for use in home care applications (cleaning or treatment of flooring, tatami, kitchen stoves and fans, etc.), car care applications (cleaning and waxing), facial and body skin care applications (cleansing, sterilizing, moisturizing, and make-up removal), and pet care applications (e.g., brushing). The heat generating shaped article of the present invention is suitably used in the warming article for the above-described applications.

The present invention will now be illustrated in greater detail with reference to Examples.

Warming articles were prepared in Examples 1-1 to 1-4 and Comparative Example 1-1. The duration of the heat at 40° C. or higher, the maximum temperature reached, and the amount of generated water vapor of the resulting heat generating sheets and the expansion properties of the resulting warming articles were measured and evaluated in accordance with the methods previously described. The results obtained are shown in Table 1-1.

Heat generating intermediate sheets having the composition shown in Table 2-1 were prepared in Examples 2-1 to 2-3 and Comparative Example 2-1. The maximum stress and the breaking elongation of the resulting heat generating intermediate sheet while dry and the maximum stress and the breaking elongation of the resulting heat generating sheet (after impregnation of electrolytic solution) were measured by the methods described above. The resulting heat generating intermediate sheet was combined with other sheet materials as described below, and the resulting multilayer structure was heat pressed to form projections as described below, and cut to shape to prepare a warming article 21. The projection forming properties were evaluated by visual observation. The results of measurement and evaluation are shown in Table 2-2.

EXAMPLE 1-1

Formulation of Raw Material Composition:
Oxidizable metal: iron powder (RKH from Dowa Iron Powder Co., Ltd. 75 wt %
Fibrous material: pulp fiber NBKP (Mackenzie from Fletcher Challenge Canada, Ltd.; CSF: 200 ml) 10 wt %
Moisture retaining agent: activated carbon (TAIKO SA1000 from Futamura Chemical Co., Ltd.; average particle size: 10 µm) 15 wt %
Flocculant (the amount is based on 100 parts by weight of a mixture of the above components):
    sodium carboxymethyl cellulose (Cellogen WS-C from Dai-ichi Kogyo Seiyaku Co., Ltd.) 0.2 parts
    polyamide-epichlorohydrin resin (WS552 from Japan PMC Corp.) 0.3 parts
Water (industrial water), added to give a solids content of 0.3%
Papermaking Conditions:
    The above raw material composition was formed into a sheet on an inclined short-wire paper machine to prepare a wet molded sheet.
Drying Conditions:
    The wet molded sheet was dewatered between felt blankets, passed as such between 120° C. heated rolls to be dried to a water content of 5 wt % or less to obtain a molded sheet (heat generating intermediate sheet) having a basis weight of 180 g/m$^2$ and a thickness of 0.25 mm. As a result of measurement with a thermogravimetric analyzer (TG/DTA 6200 from Seiko Instruments Inc.), the resulting heat generating intermediate sheet was found to be made up of 69 wt % iron, 19 wt % pulp, and 12 wt % activated carbon.
Conditions of Electrolytic Solution Addition:
    The resulting dried sheet (heat generating intermediate sheet) was coated with an electrolytic solution described below to make a molded sheet (heat generating sheet) containing 60 parts by weight of the electrolytic solution per 100 parts by weight of the heat generating intermediate sheet.
Electrolytic Solution:
    Electrolyte: purified salt (NaCl)
    Water: industrial water
    Concentration: 5% by mass
    The resulting heat generating sheet consisted of iron 43.1 wt %, pulp 11.9 wt %, activated carbon 7.5 wt %, NaCl 1.9 wt %, and water 35.6 wt %.
Preparation of Warming Article:
    Three cut sheets (50 mm by 50 mm) of the heat generating sheet were stacked, and an air permeable sheet (synthetic polyethylene sheet having a moisture permeability of 4.482 kg/(m$^2$·24 hr), an air permeability of 53 sec/100 ml, and a basis weight of 40 g/m$^2$) and an air impermeable sheet (polyethylene sheet having a basis weight of 20 g/m$^2$) were superposed on one side and the other side of the stack, respectively. The periphery around the edges of the heat generating sheets was united by heat sealing to obtain a warming article (heat generating main body).

EXAMPLE 1-2

A warming article was prepared in the same manner as in Example 1-1, except for replacing the air permeable sheet with an air-permeable, porous polyethylene sheet having a water vapor permeability of 5.114 kg/(m²·24 hr), an air permeability of 484 sec/100 ml, and a basis weight of 36 g/m².

EXAMPLE 1-3

A warming article was prepared in the same manner as in Example 1-1, except for replacing the air permeable sheet with an air-permeable, melt-blown polypropylene nonwoven fabric having a water vapor permeability of 4.357 kg/(m²·24 hr), an air permeability of 0 sec/100 ml, and a basis weight of 30 g/m².

EXAMPLE 1-4

A warming article was prepared in the same manner as in Example 1-1, except for replacing the air permeable sheet with an air-permeable, porous polyethylene sheet having a water vapor permeability of 1.124 kg/(m²·24 hr), an air permeability of 5043 sec/100 ml, and a basis weight of 50 g/m².

COMPARATIVE EXAMPLE 1-1

A warming article was prepared in the same manner as in Example 1-1, except for replacing the air permeable sheet with an air-permeable, porous polyethylene sheet having a water vapor permeability of 0.359 kg/(m²·24 hr), an air permeability of 28840 sec/100 ml, and a basis weight of 90 g/m².

TABLE 1-1

|  | Example | | | | Comp. Example |
|---|---|---|---|---|---|
|  | 1-1 | 1-2 | 1-3 | 1-4 | 1-1 |
| Intermediate Sheet Composition (wt %): | | | | | |
| Oxidizable metal | 69 | 69 | 69 | 69 | 69 |
| Fibrous Material | 19 | 19 | 19 | 19 | 19 |
| Moisture-Retaining Agent | 12 | 12 | 12 | 12 | 12 |
| Air Permeable Sheet of Holder: | | | | | |
| Water Vapor Permeability (g/m²) | 4482 | 5114 | 4357 | 1124 | 359 |
| Air Permeability (sec/100 ml) | 53 | 484 | 0 | 5043 | 28840 |
| Heat Generating Sheet: | | | | | |
| Number of Sheets | 3 | 3 | 3 | 3 | 3 |
| Weight (g/m²) | 860 | 860 | 860 | 860 | 860 |
| Warming Articles (Heat Generating Main Body): | | | | | |
| 40° C. or Higher Heating Duration (min) | 6 | 6 | 6 | 37 | 0 |
| Maximum Temp. Reached (° C.) | 69.9 | 59.3 | 56.7 | 44.4 | 31.5 |
| 10-Min Cumulative Amount of Water Vapor (mg) | 359 | 344 | 395 | 41 | 18 |
| Amount of Water Vapor (mg/(cm² · 10 min)) | 14.4 | 13.8 | 15.8 | 1.65 | 0.72 |
| Volume Expansion Ratio | 2 | 6.5 | 1 | 1 | 1 |

Water Vapor Permeable Sheet:
  Example 1-1: synthetic polyethylene (PE) sheet
  Example 1-2: porous PE sheet
  Example 1-3: melt-blown polypropylene nonwoven
  Example 1-4: porous PE sheet
  Comparative Example 1-1: porous PE sheet As shown in Table 1-1, it was possible in Examples to prepare warming articles with varied characteristics of heat and water vapor generation, i.e., of the type that heats up rapidly and expands while generating enough water vapor, the type that expands at an increased ratio, the type that heats up rapidly while generating enough water vapor without being accompanied by expansion, and the type that continues generating heat at a relatively low temperature for a long duration while gradually releasing water vapor. In contrast, the warming article of Comparative Example was insufficient in both temperature and water vapor generation.

EXAMPLE 2-1

Formulation of Raw Material Composition:
Oxidizable metal: iron powder (RKH from Dowa Iron Powder Co., Ltd. 7.5 g
Fibrous material: pulp fiber NBKP (Skeena (trade name) produced by Skeena) 1.0 g
Moisture-retaining agent: activated carbon (Carboraffin (trade name) from Takeda Chemical Industries, Ltd.; under 45 μm mesh) 1.5 g
Water: industrial water 1490 g
Papermaking Conditions:
  The above raw material composition (the CSF of the pulp fiber was adjusted to 300 ml) was formed into a wet heat generating intermediate sheet using a standard sheet machine specified in JIS P8209.
Dewatering and Drying Conditions:
  The resulting molded sheet was dried between 140° C. drying rolls specified in JIS P8209 to obtain a heat generating intermediate sheet having a water content of 3% or less.
Step of Stacking:
  An air permeable sheet and an air impermeable sheet, both described below, were superposed on the upper and the lower sides of the heat generating intermediate sheet, respectively, and the periphery around the edges of the heat generating sheet was heat-sealed.
Air Permeable Sheet:
PET nonwoven fabric base sheet laminated on its lower side with a PE/CaCO₃ mixed, porous sheet; thickness: 25 μm; water vapor permeability: 1000 g/(m²·24 hr)
Air Impermeable Sheet:
PET nonwoven fabric base sheet laminated with a PE film; thickness: 100 μm
Heat Pressing:
  The resulting multilayer sheet was heat pressed under the following conditions into a shape having the following geometry.
Heat press mold: Labo Press 10T, manufactured by Toyo Seiki Seisaku-Sho, Ltd.
Heat pressing temperature: 110° C.
Heat pressing pressure: 2 MPa
Heat pressing time: 15 seconds
Geometry of Warming Article:
  Base thickness t: 2 mm
  Projection height: 8 mm
  Projection diameter at the foot: 5 mm
Conditions of Electrolytic Solution Addition:
  A 1 mm diameter syringe was inserted into the heat-pressed multilayer sheet from the side to inject an electrolytic solution described below into the heat generating intermediate sheet to provide a heat generating sheet having a water content of 30%. Thereafter, the side was heat sealed to obtain a warming article.
Electrolytic Solution:
  Electrolyte: purified salt (NaCl)
  Water: industrial water
  Concentration: 3 wt %

EXAMPLE 2-2

A heat generating intermediate sheet was prepared as follows and combined with other sheets in the same manner as in Example 2-1. The resulting multilayer sheet was heat pressed to form projections, cut to shape, and impregnated with an electrolytic solution in the same manner as in Example 2-1 to obtain a warming article.

Formulation of Raw Material Composition:
Oxidizable metal: iron powder (RKH from Dowa Iron Powder Co., Ltd.; under 45 μm mesh) 150 g
Fibrous Material:
Pulp fiber NBKP (Skeena (trade name) produced by Skeena; average length: 2.1 mm; CSF: 300 ml) 20 g
Polyvinyl alcohol fiber (VPB 107-1 (trade name) from Kuraray Co., Ltd.) 2.0 g
Moisture-retaining agent: activated carbon (Carboraffin (trade name) from Takeda Chemical Industries, Ltd.; under 45 μm mesh) 30 g
Flocculant:
Sodium carboxymethyl cellulose (Cellogen WS-C from Daiichi Kogyo Seiyaku Co., Ltd.) 0.5 g
polyamide-epichlorohydrin resin (WS547 from Japan PMC Corp.) 0.5 g
Water: industrial water 99800 g
Papermaking Conditions:
The above raw material composition was formed into a wet heat generating intermediate sheet using an inclined short-wire paper machine (possessed by Kochi Prefectural Paper Technology Center) at a line speed of 7 m/min.
Dewatering and Drying Conditions:
The resulting sheet was dewatered by squeezing between felt blankets and dried between 120° C. drying rolls at a line speed of 7 m/min to a water content of 5 wt % or less.

EXAMPLE 2-3

A heat generating intermediate sheet was prepared in the same manner as in Example 2-2, except for using a raw material composition of the following formulation. The resulting heat generating intermediate sheet was combined with other sheets in the same manner as in Example 2-1. The resulting multilayer structure was heat pressed to form projections, cut to shape, and impregnated with an electrolytic solution in the same manner as in Example 2-1 to obtain a warming article.

Formulation of Raw Material Composition:
Oxidizable metal: iron powder (RKH from Dowa Iron Powder Co., Ltd.; under 45 μm mesh) 116 g
Fibrous Material:
pulp fiber NBKP (Skeena (trade name) produced by Skeena; average length: 2.1 mm; CSF: 300 ml) 60 g
Polyvinyl alcohol fiber (VPB 107-1 (trade name) from Kuraray Co., Ltd.) 2.0 g
Moisture-retaining agent: activated carbon (Carboraffin (trade name) from Takeda Chemical Industries, Ltd.; under 45 μm mesh) 24 g
Flocculant:
Sodium carboxymethyl cellulose (Cellogen WS-C from Daiichi Kogyo Seiyaku Co., Ltd.) 0.5 g
polyamide-epichlorohydrin resin (WS547 from Japan PMC Corp.) 0.5 g
Water: industrial water 99800 g

COMPARATIVE EXAMPLE 2-1

A warming article was prepared in the same manner as in Example 2-1, except for changing the CSF of pulp to 720 ml.

TABLE 2-1

| | | Slurry Composition on Solid Basis (wt %) | | | CSF of Pulp (ml) | Components other than Fibrous Material (wt %) |
|---|---|---|---|---|---|---|
| | | Oxidi-zable Metal | Fibrous Material | Moisture Retaining Agent | | |
| Example 2-1 | manual papermaking | 75 | 10 | 15 | 300 | 88 |
| Example 2-2 | machine papermaking | 75 | 10 | 15 | 300 | * |
| Example 2-3 | machine papermaking | 58 | 30 | 12 | 300 | * |
| Comp. Example 2-1 | manual papermaking | 75 | 10 | 15 | 720 | 72 |

*Unmeasurable because of continuous papermaking using a paper machine.

TABLE 2-2

| | Heat Generating Intermediate Sheet (before addition of electrolytic solution) | | Heat Generating Sheet (after addition of electrolytic solution) | | Forma-bility of Pro-jections |
|---|---|---|---|---|---|
| | Max. Stress (MPa) | breaking elongation (%) | Max. Stress (MPa) | breaking elongation (%) | |
| Example 2-1 | 1.43 | 1.53 | 0.661 | 2.79 | good |
| Example 2-2 | 5.20 | 2.15 | 1.34 | 3.2 | good |
| Example 2-3 | 8.00 | 3.2 | 2.34 | 4.93 | good |
| Comp. Example 2-1 | 0.09 | 0.61 | 0.155 | 1.58 | break |

As shown in Table 2-1, the heat generating intermediate sheets and the heat generating sheets used in Examples 2-1 to 2-3 are excellent in maximum stress and breaking elongation. Therefore, the warming articles of Examples 2-1 to 2-3 are free from breaks, wrinkles, and non-uniformity in their projections, undergo no fall-off of the powder components, and provide sufficient warmth and moisture. In contrast, the heat generating intermediate sheet and the heat generating sheet of the warming article of Comparative Example 2-1 have a low maximum stress and breaking elongation. As a result, a break developed in the projections, the powdered components fell off, and the heat and moisture generation was insufficient.

INDUSTRIAL APPLICABILITY

The present invention provides a novel warming article that is pleasant to touch, conformable to a part of a body, and suited for a wide variety of applications.

The present invention also provides a heat generating shaped article having a precise three-dimensional shape applicable to various uses, a warming article having the heat generating shaped article, and a method of producing the warming article.

The invention claimed is:

1. A heat generating, shaped article prepared by three-dimensionally shaping a molded sheet, the molded sheet comprising:
   an oxidizable metal,
   a moisture-retaining agent, and
   a fibrous material and
   having a maximum stress of 0.3 to 5 MPa and a breaking elongation of 2.0 to 10%, the molded sheet disposed between an air permeable sheet and an air impermeable sheet and three-dimensionally shaped together with the air permeable sheet and the air impermeable sheet to form individual projections.

2. The heat generating, shaped article according to claim 1, wherein the molded sheet has, in its dried state, a maximum stress of 0.5 to 15 MPa and a breaking elongation of 0.8 to 5%.

3. The heat generating, shaped article according to claim 1, wherein the molded sheet is a sheet molded by papermaking.

4. The heat generating, shaped article according to claim 1, wherein the molded sheet contains at least 50% by weight of components other than the fibrous material while dry.

5. The heat generating, shaped article according to claim 1, wherein the fibrous material has a CSF of 600 ml or less.

6. A method of producing a warming article, the method comprising:
   incorporating an electrolyte into a heat generating sheet, the heat generating sheet including an oxidizable metal, a moisture-retaining agent and a fibrous material, and having a maximum stress of 0.3 to 5 MPa and a breaking elongation of 2.0 to 10%; and
   three-dimensionally shaping the heat generating sheet, including disposing the heat generating sheet between an air permeable sheet and an air impermeable sheet so as to be three-dimensionally shaped together with the air permeable sheet and the air impermeable sheet so as to form individual projections.

* * * * *